US009238046B2

(12) United States Patent
Gorman et al.

(10) Patent No.: US 9,238,046 B2
(45) Date of Patent: Jan. 19, 2016

(54) PREVENTION OF INFARCT EXPANSION

(75) Inventors: Robert C. Gorman, Lower Gwynedd, PA (US); Joseph H. Gorman, III, Lower Gwynedd, PA (US); Liam P. Ryan, Boston, MA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 945 days.

(21) Appl. No.: 12/679,147

(22) PCT Filed: Sep. 19, 2008

(86) PCT No.: PCT/US2008/077011
§ 371 (c)(1), (2), (4) Date: Mar. 1, 2012

(87) PCT Pub. No.: WO2009/039368
PCT Pub. Date: Mar. 26, 2009

(65) Prior Publication Data

US 2012/0148630 A1 Jun. 14, 2012

Related U.S. Application Data

(60) Provisional application No. 60/974,154, filed on Sep. 21, 2007.

(51) Int. Cl.

| | |
|---|---|
| ***A61K 9/00*** | (2006.01) |
| ***A61K 33/42*** | (2006.01) |
| ***A61L 27/10*** | (2006.01) |
| ***A61L 27/12*** | (2006.01) |
| ***A61L 27/50*** | (2006.01) |

(52) U.S. Cl.
CPC ............... *A61K 33/42* (2013.01); *A61K 9/0019* (2013.01); *A61L 27/10* (2013.01); *A61L 27/12* (2013.01); *A61L 27/50* (2013.01); *A61L 2400/06* (2013.01); *A61L 2430/20* (2013.01)

(58) Field of Classification Search
CPC ...... A61K 33/42; A61K 9/0019; A61L 27/10; A61L 27/12; A61L 27/50; A61L 2400/06; A61L 2430/20
See application file for complete search history.

(56) References Cited

U.S. PATENT DOCUMENTS

| | | | | |
|---|---|---|---|---|
| 5,648,097 | A * | 7/1997 | Nuwayser | 424/489 |
| 6,558,612 | B1 * | 5/2003 | Hubbard | 264/654 |
| 7,311,731 | B2 | 12/2007 | Lesniak et al. | |
| 2002/0188170 | A1 * | 12/2002 | Santamore et al. | 600/37 |
| 2003/0054995 | A1 | 3/2003 | Carmeliet | |
| 2003/0120204 | A1 | 6/2003 | Unger et al. | |
| 2004/0193138 | A1 | 9/2004 | Levin et al. | |
| 2005/0232902 | A1 | 10/2005 | Kofidis | |
| 2005/0271631 | A1 | 12/2005 | Lee et al. | |
| 2006/0135912 | A1 | 6/2006 | Chernomosky et al. | |
| 2006/0229492 | A1 | 10/2006 | Gelfand et al. | |
| 2007/0014784 | A1 | 1/2007 | Nayak et al. | |
| 2007/0042016 | A1 | 2/2007 | Nayak et al. | |
| 2007/0093748 | A1 | 4/2007 | Nayak et al. | |
| 2007/0233219 | A1 | 10/2007 | Shafi et al. | |
| 2008/0269720 | A1 | 10/2008 | Sabbah et al. | |

FOREIGN PATENT DOCUMENTS

WO WO 2009/039368 3/2009

OTHER PUBLICATIONS

Merx MW et al. 2005. Myocardial Stiffness, Cardiac Remodeling, and Diastolic Dysfunction in Calcification-Prone Fetuin-A-Deficient Mice. J Am Soc Nephrol.; 16: 3357-3364.*

Ahn, "Calcium Hydroxylapatite: Radiesse", Facial Plast. Surg. Clin. N. Am., Feb. 2007, 15(1), 85-90.

Blom et al., "A Cardiac Support Device Modifies Left Ventricular Geometry and Myocardial Structure After Myocardial Infarction", Circulation, Aug. 30, 2005, 112(9), 1274-1283.

Bolognese et al., "Impact of Microvascular Dysfunction on Left Ventricular Remodeling and Long-Term Clinical Outcome after Primary Coronary Angioplasty for Acute Myocardial Infarction", Circulation, Mar. 9, 2004, 109(9), 1121-1126.

Bolognese et al., "Left ventricular remodeling after primary coronary angioplasty: patterns of left ventricular dilation and long-term prognostic implications", Circulation, Oct. 29, 2002, 106(18), 2351-2357.

Dai et al., "Thickening of the infracted wall by collagen injection improves left ventricular function in rats: a novel approach to preserve cardiac function after myocardial infarction", J Am Coll Cardiol, Aug. 16, 2005, 46(4), 714-719.

Drobeck et al., "Histologic observation of soft tissue responses to implanted, multifaceted particles and discs of hydroxy lapatite", J Oral Maxillofac Surg., Mar. 1984, 42(3), 143-149.

Eaton et al., "Regional cardiac dilatation after acute myocardial infarction", N Engl. J Med Jan. 11, 1979, 300(2), 57-62.

Ellis et al., "Review of Non-FDA-Approved Fillers", Facial Plast. Surg. Clin. N. Am., May 2007, 15(2), 239-246.

Enomoto et al., "Early ventricular restraint after myocardial infarction: the extent of the wrap determines the outcome of remodeling", Ann Thorac Surg., Mar. 2005, 79(3), 881-887.

Epstein et al., "MR tagging early after myocardial infarction in mice demonstrates contractile dysfunction in adjacent and remote regions", Magn Reson Med, Aug. 2002, 48(2), 399-403.

Erlebacher et al., "Early dilation of the infarcted segment in acute transmural myocardial infarction: role of infarct expansion in acute left ventricular enlargement", J Am Coll Cardiol Aug. 1984, 4(2), 201-208.

Force et al., "Acute reduction in functional infarct expansion with late coronary reperfusion: assessment with quantitative two-dimensional echocardiography", J Am Coll Cardiol, Jan. 1988, 11(1), 192-200.

(Continued)

*Primary Examiner* — Johann R Richter
*Assistant Examiner* — David Browe
(74) *Attorney, Agent, or Firm* — Baker & Hostetler LLP

(57) ABSTRACT

Provided are methods and kits for safe and effective therapy that can be administered early after a heart attack in order to prevent progressive heart dilatation and resultant loss of function. The therapy includes the administration of particulate compositions to a region comprising an infarct or a portion thereof.

13 Claims, 12 Drawing Sheets

(56) References Cited

OTHER PUBLICATIONS

Fox et al., "Decline in Rates of Death and Heart Failure in Acute Coronary Syndromes 1999-2006", JAMA, Mar. 2, 2007, 297(17), 1892-1900.

Gheorghiade et al., "Chronic heart failure in the United States: a manifestation of coronary artery disease", Circulation, Jan. 27, 1998, 97(3), 282-289.

Gupta et al., "Changes in passive mechanical stiffness of myocardial tissue with aneurysm formation", Circulation, May 1994, 85(5), 2315-2326.

Havlik, "Hydroxyapatite", Plast Reconstr Surg., Sep. 15, 2002, 110(4), 1176-1179.

Hobar et al., "Porous hydroxyapatite granules for alloplastic enhancement of the facial region", Clin Plast Surg., Oct. 2000, 27(4), 557-569.

Hochman et al., "Limitation of myocardial infarct expansion by reperfusion independent of myocardial salvage", Circulation, Jan. 1987, 75(1), 299-306.

Jackson et al., "Border zone geometry increases wall stress after myocardial infarction: contrast echocardiographic assessment", Am J Physiol, Feb. 2003, 284(2), H475-H479.

Jackson et al., "Extension ofborderzone myocardium in postinfarction dilated cardiomyopathy", J Am Coll Cardiol, Sep. 18, 2002, 40(6), 1160-1167.

Jawad et al., "Myocardial tissue engineering", British Medical Bulletin, Sep. 2008, 87, 31-47.

Kanchwala et al., "Reliable Soft Tissue Augmentation: A Clinical Comparison of Injectable Soft-Tissue Fillers for Facial-Volume Augmentation", Annals of Plastic Surgery, Jul. 2005, 55(1), 30-35.

Kelley et al., "Restraining infarct expansion preserves left ventricular geometry and function after acute anteroapical infarction", Circulation, Jan. 5-12, 1999, 99(1), 135-142.

Kramer et al., "Regional differences in function within noninfarcted myocardium during left ventricular remodeling", Circulation, Sep. 1993, 88(3), 1279-1288.

Landa et al., "Effect of injectable alginate implant on cardiac remodeling and function after recent and old infarcts in rats", Circulation, Mar. 18, 2008, 117(11), 1388-1396.

Lima et al., "Impaired thickening of nonischemic myocardium during acute regional ischemia in the dog", Circulation, May 1985, 71(5), 1048-1059.

Markovitz et al., "Large animal model of left ventricular aneurysm", Ann Thorac Surg, Dec. 1989, 48(6), 838-845.

Moainie et al., "Infarct restraint attenuates ischemic mitral regurgitation following posterolateral infarction", Ann Thorac Surg., Aug. 2002, 74(2), 444-449.

Pilla et al., "Early post infarction ventricular restraint improves borderzone wall thickening dynamics during remodeling", Ann Thorac Surg., Dec. 2005, 80(6), 2257-2262.

Ratcliffe, "Non ischemic infarct expansion", J Am Coll Cardiol, Sep. 18, 2002, 40(6), 1168-1171.

Ryan et al., "Abstract 2460: Dermal Filler Injection: A Novel Approach for Preventing Infarct Expansion and Ventricular Remodeling", Circulation, William W. L. Glenn Lecture, Oct. 16, 2007, 116:II_541.

Ryan et al., "Dermal Filler Injection: A novel approach for limiting infarct expansion", Ann Thorac Surg, Jan. 2009, 87(1), 148-155.

Sherman et al., "Catheter-based delivery of cells to the heart", Nat Clin Pract Cardiovasc Med, Mar. 2006, 3(Suppl. 1), S57-S64.

Shimizu, "Subcutaneous tissue response in rats to injection of fine particles of synthetic hydroxyapatite ceramic", Biomed Res, Jan. 1988, 9(2), 95-111.

Tzikas, "Evaluation of the Radiance FN soft tissue filler for facial soft tissue augmentation", Arch Facial Plast Surg., Jul.-Aug. 2004, 6(4), 234-239.

Wang et al., "Novel thermosensitive hydrogel injection inhibits post-infarct ventricle remodeling", Euro J of Heart Failure, Jan. 2009, 11(1), 14-19.

Weisman et al., "Myocardial infarct expansion, infarct extension, and reinfarction: pathophysiologic concepts", Prog Cardiovasc Dis, Sep.-Oct. 1987, 30(2), 73-110.

Yu et al., "Restoration of left ventricular geometry and improvement of left ventricular function in a rodent model of chronic ischemic cardiomyopathy", J Thorac Cardiovasc Surg, Jan. 2009, 137(1), 180-187.

* cited by examiner

PREVENTION OF INFARCT EXPANSION

CROSS-REFERENCE TO RELATED APPLICATIONS

This application is the national stage entry of PCT/US2008/077011, filed Sep. 19, 2008, which claims the benefit of priority to U.S. Provisional Patent Application Ser. No. 60/974,154, filed Sep. 21, 2007, each of which is herein incorporated by reference in its entirety.

GOVERNMENT RIGHTS

The United States Government may have rights in the invention described herein, which was made in part with funding from the National Institutes of Health, Grant Nos. HL63954 and HL71137 to Robert C. Gorman, HL76560 to Joseph H. Gorman, III, from the American Heart Association, Post-Doctoral Fellowship No. 0625455U to Robert C. Gorman and Liam P. Ryan, and from individual Established Investigator Awards from the American Heart Association to Robert C. Gorman and Joseph H. Gorman, III.

FIELD OF THE INVENTION

The present invention relates to systems and methods for the treatment of patients following myocardial infarction, and more particularly, for the regulation of post infarct cardiac expansion.

BACKGROUND OF THE INVENTION

Five million Americans suffer from heart failure and 250,000 die from the disease each year. Left ventricular (LV) remodeling caused by a myocardial infarction (MI) is now responsible for almost 70% of the 5 million cases of heart failure in the United States. Gheorghiade M, Bonow R O. *Chronic heart failure in the United States: a manifestation of coronary artery disease. Circulation* 1998; 97:282-289. In most cases patients who survive a myocardial infarction are initially asymptomatic, however, many develop progressive heart enlargement, loss of heart function and symptoms of heart failure over the ensuing months and years after their initial heart attack. This progressive process is termed ventricular remodeling. In spite of modern medical and surgical treatment the 5 and 8 year mortality after symptoms of heart failure develop is 50% and 80%, respectively.

Immediately after a heart attack the affected region of heart muscle stops contracting and stretches as the remainder of the heart continues to contract. This stretching is termed infarct expansion. Early infarct expansion, or stretching, has been associated with adverse remodeling and a poor long-term prognosis. Erlebacher J A et al., *Early dilation of the infarcted segment in acute transmural myocardial infarction: role of infarct expansion in acute left ventricular enlargement. J Am Coll Cardiol* 1984; 4:201-208; Eaton L W et al., *Regional cardiac dilatation after acute myocardial infarction. N Engl J Med* 1979; 300:57-62; Weisman H F, Healy B. *Myocardial infarct expansion, infarct extension, and reinfarction: pathophysiologic concepts. Prog Cardiovasc Dis* 1987; 30:73-110. In previous experimental studies using sonomicrometry (Jackson B M et al., *Extension of borderzone myocardium in postinfarction dilated cardiomyopathy. J Am Coll Cardiol* 2002; 40:1160-1167), echocardiography (Lima J A et al., *Impaired thickening of nonischemic myocardium during acute regional ischemia in the dog. Circulation* 1985; 71:1048-1059; Jackson B M, et al. *Border zone geometry increases wall stress after myocardial infarction: contrast echocardiographic assessment. Am J Physiol* 2003; 284: H475-H479), and magnetic resonance imaging (Kramer C M et al., *Regional differences in function within noninfarcted myocardium during left ventricular remodeling. Circulation* 1993; 88:1279-1288; Epstein F H et al., *MR tagging early after myocardial infarction in mice demonstrates contractile dysfunction in adjacent and remote regions. Magn Reson Med* 2002; 48: 399-403; Pilla J J et al., *Early post infarction ventricular restraint improves borderzone wall thickening dynamics during remodeling. Ann Thorac Surg* 2005; 80:2257-2262), infarct expansion has been shown to result in stretching and decreased contractile function in the neighboring normally perfused borderzone (BZ) myocardium. Additionally, while the perfused but hypocontractile myocardium is initially isolated to the region immediately adjacent to the infarct, the process extends with time to involve progressively more myocardium remote from the infarcted region. Jackson B M et al. (2002); Ratcliffe M B. *Non ischemic infarct expansion. J Am Coll Cardiol* 2002; 40: 1168-1171.

Thus, infarct expansion initiates and sustains the progression to symptomatic heart failure. A safe and effective therapy that could be deployed early after a heart attack which could prevent progressive heart dilatation and loss of function would be of great value.

Currently patients who suffer a heart attack are treated with medications such as beta adrenergic blockers, angiotensin converting enzyme inhibitors and angiotensin receptor blockers. These classes of drugs have modest beneficial effects on survival that tend to deteriorate over time. Improved drug and device based treatments are, therefore, being sought aggressively. Cell therapy treatments could yield positive results; however, while significant advances have been made in cardiac cell therapy, definitive therapeutic benefits have been difficult to demonstrate conclusively despite numerous clinical trials.

Certain mechanical means for restraining the size of the heart have been developed. Acorn Cardiovascular, Inc. (St. Paul, Minn.) has developed a mesh restraint device for wrapping the heart in patients with established heart failure. This product requires major surgery for placement and has failed to gain FDA approval. It has never been placed clinically in the early postinfarction period. Paracor Medical Inc. (Sunnyvale, Calif.) has developed a nitinol mesh for restraining the heart. Like the device developed by Acorn Cardiovascular, this product requires surgical placement and is intended for patients with established heart failure. The Paracor device is in phase II clinical trials.

Methods that involve the injection of blood plasma and cellular derivatives in order to provide (or induce) structural reinforcement for injured cardiac tissue are disclosed by Nayak et al. in U.S. Pub. No. 2007/0093748. Nayak et al. used platelet rich plasma, alone or in a gelled combination with clotting agents, to ameliorate cardiac remodeling.

There remains an unmet need for systems and methods for the regulation of post-infarct cardiac expansion other than cell therapy regimens, mesh restraint devices, and injection of blood plasma and cellular derivatives.

SUMMARY OF THE INVENTION

In one aspect, provided are methods for the stabilization of cardiac infarct tissue comprising placing in the cardiac infarct tissue a composition comprising a particulate, biologically compatible, inorganic material in an amount effective to improve or prevent the deterioration of at least one hemodynamic parameter probative of cardiac stability.

Also provided are methods for the stabilization of cardiac infarct tissue comprising placing in the cardiac infarct tissue a composition comprising a particulate, biologically compatible, inorganic material in an amount effective to reduce the likelihood of cardiac remodeling.

The present invention is also directed to methods for reducing post-infarct cardiac remodeling comprising increasing the volume of a cardiac infarct tissue wall via injection of a volume-increasing material into said cardiac infarct tissue, and maintaining substantially all of said material within said cardiac infarct tissue for an extended period of time following said injection.

In another aspect, disclosed are kits for use in the stabilization of cardiac infarct tissue comprising a composition comprising a particulate, biologically compatible, inorganic material and an injection tool capable of delivering said composition to a region comprising an infarct or a portion thereof within a living patient.

BRIEF DESCRIPTION OF THE DRAWINGS

The summary, as well as the following detailed description, is further understood when read in conjunction with the appended figures. For the purpose of illustrating the invention, there are shown in the figures exemplary embodiments of the invention; however, the invention is not limited to the specific methods, compositions, and devices disclosed.

DETAILED DESCRIPTION OF ILLUSTRATIVE EMBODIMENTS

Figure 1:
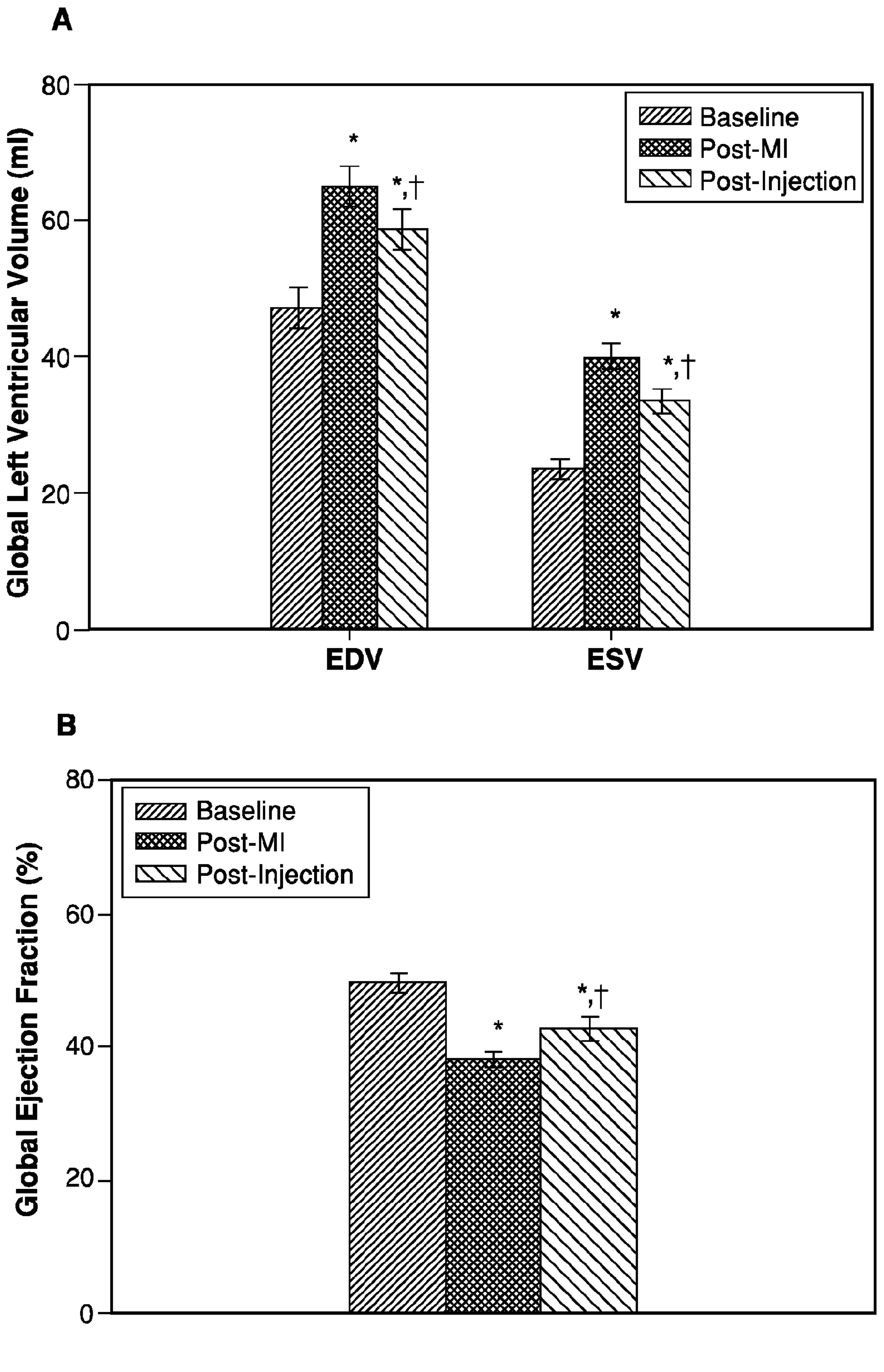
FIG. 1 provides left ventricular global end diastolic volumes (EDV) and end systolic volumes (ESV) at baseline, 30 minutes after infarction, and 15 minutes after injection with filler material, as well as corresponding ejection fraction data.

In the present disclosure the singular forms "a," "an," and "the" include the plural reference, and reference to a particular numerical value includes at least that particular value, unless the context clearly indicates otherwise. Thus, for example, a reference to "a material" is a reference to one or more of such materials and equivalents thereof known to those skilled in the art, and so forth.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As provided herein, it has been discovered that certain compositions, including dermal (or soft tissue) fillers that are currently used in plastic surgery, can thicken the infarct region, limit its expansion, reduce global heart dilatation, and provide long-term structural and functional benefits. The instant methods and kits provide safe and effective therapy that can be administered early after a heart attack in order to prevent progressive heart dilatation and loss of function. The value of such a therapeutic modality is further increased in that the compositions can be delivered via a minimally invasive (e.g., catheter based) approach that does not require invasive surgery, as contrasted with existing mechanical means for regulating heart size following myocardial infarction, such as heart mesh devices. The inventive kits and methods also reduce likelihood of the necessity for multiple episodes of treatment.

In contrast with existing methods for treating infarcted cardiac tissue, the present invention can involve the injection of particulate, biologically compatible, inorganic/acellular material in an amount effective to reduce the likelihood of cardiac remodeling, to improve at least one hemodynamic parameter probative of cardiac stability, or both. As used herein, "particulate" refers to the presence of discrete solid or semisolid particles within the material. Such particles may comprise microstructures, such as microspheres. As used herein, "inorganic" includes certain, limited classes of materials that, although strictly speaking are organic, possess properties suitable for use in the practice of the present invention. For purposes of this invention, such materials are denominated quasi-inorganic but fall within the rubric of "inorganic" materials, examples of which include, but are not limited to, dextran.

The present methods are also directed to reducing post-infarct cardiac remodeling by increasing the volume of a cardiac infarct tissue wall via injection of a volume-increasing material into said cardiac infarct tissue, and maintaining substantially all of said material within said cardiac infarct tissue for an extended period of time following said injection. The maintenance of volume-increasing material within cardiac infarct tissue for an extended period of time provides beneficial effects that extend far beyond that which was possible in accordance with previously-known techniques, and reduces the likelihood that patients will be required to undergo several repetitions of treatment with respect to a given injury.

Prior methods, for example, those disclosed in U.S. Pub. No. 2007/0093748 to Nayak et al. ("the Nayak publication"), make use of organic injectates to provide structural reinforcement and, in some instances, introduce biologically-active agents, in order to provide treatment for infarcted or otherwise injured cardiac tissue. The Nayak publication discloses that biologically-active platelet rich plasma or autologous platelet gel can be injected into ischemic myocardium tissue to thicken the ventricle wall and reduce one cardiac volume parameter (viz., diastolic volume) and one hemodynamic parameter (ejection fraction). See Nayak publication at paragraphs [0243]-[0249]. Although it is not definitely known how autologous platelet gel functions to improve some characteristics of infarcted tissue, one route of action may be the induction of a nonspecific inflammatory response, although the properties of autologous platelet gel are highly variable among patients and within a single patient over time. Additionally, autologous platelet gel does not persist within the infarct tissue for more than a few weeks following injection; any immediate improvement after injection is probably due to a transient bulking effect in the infarct.

The present invention represents a significant improvement over the methods taught by such prior methods. For example, the materials used for the instant invention can ameliorate cardiac remodeling with respect to one or more volume parameters, improve at least one hemodynamic parameter, increase the stiffness of treated tissue, and, due to, inter alia, their particularized physical characteristics, maintain a high level of durability and efficacy once placed in situ. The durability of the particulate, inorganic materials used for the present invention provides prolonged stabilization of the perfused myocardial regions. Furthermore, the use of inorganic, acellular compositions rather than blood derivatives like platelet rich plasma or platelet gel eliminates concerns of adverse biological (e.g., immune) reaction, specialized storage requirements, and limited production capacity. The prior art likewise does not provide methods that reduce the necessity for repeat intervention following an initial treatment. The Nayak publication makes use of autologous platelet gel (APG), i.e., platelet rich plasma prepared from the subject's own blood combined with clotting agents, to avoid the possibility of an immune reaction, but this strategy necessitates a complex, costly, and time-consuming process of preparing an injectate from substances derived from the subject himself, and cannot provide the basis for a universal, ready-to-use process or kit that can be employed on extremely short notice following myocardial infarction. Furthermore, the materials used in connection with the present invention do not require mixing or combination with an activating reagent (such as thrombin, to induce coagulation) immediately prior to injection. In contrast, autologous platelet gel must be mixed with thrombin or one or more other activating agent(s) prior to injection in order to provide the intended effects.

The present invention addresses the urgent need for ways to attenuate heart remodeling and improve or prevent the deterioration of hemodynamic parameters following infarction. Provided are methods for the stabilization of cardiac infarct tissue comprising placing in the cardiac infarct tissue a composition comprising a particulate, biologically compatible, inorganic material in an amount effective to improve at least one hemodynamic parameter probative of cardiac stability, to reduce the likelihood of cardiac remodeling, or both. Also provided are methods for reducing post-infarct cardiac remodeling comprising increasing the volume of a cardiac infarct tissue wall via injection of a volume-increasing material into said cardiac infarct tissue, and maintaining substantially all of said material within said cardiac infarct tissue for an extended period of time following said injection. Unlike earlier techniques, the instant methods may further comprise providing support structures for the growth of fibrous tissue in or near said cardiac infarct tissue.

The volume increasing material may comprise a particulate, biologically compatible, inorganic substance. Semi-resorbable materials may be used, but the period of time during which the material persists within the region or site of introduction can be up to three months, up to six months, up to one year, up to two years, up to three years, or longer. The material can be one or more synthetically-derived substance, one or more substances derived from natural sources, or any combination thereof. The particulate material may comprise particles having characteristic dimensions of about 10 μm to about 500 μm, preferably from about 20 μm to about 100 μm, and even more preferably from about 25 μm to about 50 μm. Because particles may be present in numerous configurations, including, inter alia, substantially cylindrical or substantially spherical, or otherwise, the term "characteristic dimensions" is used herein to describe a major dimension of a particle, e.g., length in the case of substantially cylindrical particles, and diameter in the case of substantially spherical particles. For example, a preferred material comprises one or more forms of calcium phosphate, such as calcium hydroxyapatite, which is commercially-available under the name Radiesse® (BioForm Medical, Inc., San Mateo, Calif.), and comprises microspherical particles that typically have characteristic dimensions of about 25 μm to about 45 μm. Additional details regarding Radiesse® are disclosed in Ahn M S, *Facial Plast Surg Clin N Am* 15 (2007) 85-90, the contents of which are incorporated herein in their entirety.

It has been discovered that the volume increasing materials of the present invention, including particulate, biologically compatible, inorganic materials, display improved durability as compared with injectate materials disclosed in the prior art, e.g., autologous platelet gel (see U.S. Pub. No. 2007/0093748). The materials of the present invention are uniquely well-suited to maintaining a lasting presence within infarct tissue and therefore to prolonging the beneficial structural effects of tissue reinforcement. The instant materials also provide the extremely beneficial effect of promoting fibrous tissue growth in and/or near damaged tissue. Not wishing to be bound by any particular theory of operation, it is believed that, following placement of a composition comprising the particulate material into the infarct tissue, dense cellular components such as fibroblasts surround the particles of the particulate material. That the present materials persist within the infarct tissue also means that patients will often not be required to undergo repeated episodes of treatment.

The present materials are preferably employed in microparticulate, e.g., microspherical, form. When microparticles are used, some or all of such microparticles may be radiopaque, so that once at least some quantity of the material has been placed in the infarct tissue, X-ray or other monitoring means may be used to determine the physical location and dispersal characteristics of the material within the tissue. The microparticles may also or alternatively be echopaque, that is, they may possess acoustic impedance properties (sometimes referred to as the characteristic of casting an "acoustic shadow"), and therefore be detectible via ultrasound or other acoustic detection methodologies. Radiopaque and/or echopaque markers may be included whether the material comprises microparticles or not. Other materials that contain microparticles may be used. For example, the material may comprise microparticles of calcium phosphate (any form, including, inter alia, calcium hydroxyapatite, tri-calcium phosphate), hyaluronic acid, dextran, polyacrylamide (for example, positively-charged polyacrylamide to attract negatively-charged native glycosaminoglycans like hyaluronic acid), polymethylmethacrylate, hydroxyethylmethacralate, other acrylics, polyvinyl, poly-L-lactic acid, silicone, glass, glass-ceramic, or plastic. Such examples are not intended to be limiting, as any biocompatible, durable, preferably microparticulate material or mixtures thereof may be used. See also Ellis D A F & Segall L, *Facial Plast Surg Clin N Am* 15 (2007) 239-246 (discussing non-FDA-approved filler materials).

The composition that is placed in the cardiac infarct tissue may additionally comprise a carrier, diluent, or excipient. Suitable examples of carriers, diluents and excipients will be readily appreciated by those skilled in the art. The carrier, excipient, or diluent can contain other desired additives such as solubilizers, emulsifiers, buffers, preservatives, suspending agents, thickening agents, colors, viscosity regulators, stabilizers, osmo-regulators, and the like. The particulate material may be present in such carrier, diluent, or excipient in the form of a solution, mixture, suspension, emulsion, or dispersion. For example, the composition may comprise a suspension of microspheres in a carrier, such as an aqueous carrier. The carrier may take the form of a gel. In one embodiment, for example, the composition comprises microspheres suspended in a gel carrier comprising water, glycerin, and carboxymethylcellulose. Other suitable gel-forming substances may be used to form the carrier, and such substances will be readily appreciated by the ordinary skilled artisan. Nonlimiting examples of carrier materials include methylcellulose, glycerin, water, hyaluronic acid, collagen, polyacrylamid, polyvinyl pyrrolidone, carboxymethylcellulose, silicone and mannitol. Individual carrier materials may be used alone or in combination with one or more other carrier materials. The carrier materials of the present invention may be bioresorbable. For example, the present volume increasing material may comprise a bioresorbable carrier and a non-resorbable particulate material, such that following placement of the volume increasing material into cardiac infarct tissue, the carrier and particulate material add immediate "bulk" to the tissue, but the carrier is absorbed over time while the particulate material persists within the tissue. As previously described, the remaining particles may promote fibrous tissue ingrowth at the situs of the previous injury. Where the material is particulate, the carrier, diluent, or excipient may function to maintain space between the particles, which can have the beneficial effect of promoting ingrowth of fibrous tissue over time. Such an effect can, among other results, help to ameliorate infarct tissue thinning that typically occurs over time following myocardial infarction. The combination of the material and carrier/diluent/excipient can therefore act as a physical scaffold that supports and/or potentiates the natural healing process, which can include the ingrowth of tissue.

The material that is placed in the infarct tissue may comprise one or more "dermal filler"-type products, whether polymeric or not, a number of which are currently commercially available. Such commercially available dermal filler products include collagen, Hylaform® (NAMED Aesthetics, Santa Barbara, Calif.), Restylane® (Medicis Aesthetics Inc., Scottsdale, Ariz.), Sculptra™ (sanofi-aventis, Paris, France), and Radiesse® (BioForm Medical, Inc., San Mateo, Calif.). Some physical and commercial properties of these materials are summarized in Table 1, below.

TABLE 1

| | Filler Material | | | | |
|---|---|---|---|---|---|
| | Collagen | Hylaform ® (hyaluronic acid) | Restylane ® (hyaluronic acid) | Sculptra ™ (poly-lactic acid) | Radiesse ® (calcium hydroxyapatite) |
| Current Use | Wrinkles, Lip Augmentation | Wrinkles, Lip Augmentation | Wrinkles, Lip Augmentation | Adding Volume To Cheeks, Other Facial Areas | Wrinkles, Lip Augmentation |
| Hypersensitivity Risk | +++ | ++ | + | + | + |
| Source | Cow Hide | Rooster Combs | Bacteria | Synthetic | Synthetic |
| Skin Testing Required | Yes | No | No | No | No |
| Durability | 3 to 6 Months | Up to 1 Year | Up to 1 Year | Up to 2 Years | 2 or More Years |
| Cost | $ | $$ | $$/$$$ | $$$$ | $$$$ |

All of the products listed in Table 1 are approved for use as dermal fillers. Plastic surgeons, dermatologists, and primary care physicians use these products primarily on the face to remove wrinkles and for lip augmentation, and some of these products are commonly used to improve continence of the urinary sphincter and to treat paralyzed vocal cords; in such contexts the methods for administration of dermal fillers and related volume-increasing materials are readily appreciated by skilled practitioners.

The materials for use in connection with the present invention may also be selected from one or more substances that have not yet been officially approved for medical use. Non-limiting examples of non-FDA-approved materials are provided in Ellis D A F & Segall L, *Facial Plast Surg Clin N Am* 15 (2007) 239-246, which is incorporated herein by reference in its entirety. Non-approved substances may be used alone or in combination with FDA-approved or otherwise medically sanctioned substances.

The composition that is placed in the infarcted tissue can further comprise a biological material. The biological material may be used to enhance the performance of the composition in terms of its delivery characteristics, its ability to provide structural support to injured cardiac tissue, its ability to biologically enhance the recovery of the damaged tissue, or both. Other nonlimiting uses for the inclusion of a biological material include increased or accelerated production of structural components such as collagen, increased or accelerated overall healing, production of a thicker scar, increased or accelerated generation of blood vessels in the healing infarct, increased or accelerated regeneration of cardiac myocytes within the infarct region, or increased or accelerated migration of fibroblasts or myofibroblasts into the infarct area. Exemplary biological materials include, but are not limited to, proteins, peptides, amino acids, growth factors, enzymes, antibodies, and hormones. Some preferred proteins include collagen, elastin, and other "structural"-type proteins. The biological material comprise cells or cell components, for example, blood cells all kinds or stem cells of all kinds, especially myoblasts, mesenchymal progenitor cells (MPCs), or mesenchymal stem cells (MSCs). The biological material may be of autologous, allogeneic, or xenologous nature. Blood cells of any kind, including platelets, are also contemplated. Further examples of biological materials include blood clotting proteins, fibrin glue, and cryoglue. The preceding examples of biological materials, as well as other biological materials that will be readily appreciated by those skilled in the art as providing beneficial effects with respect to the healing, regeneration, and/or support of damaged cardiac tissue, may be used alone or in any combination.

Any suitable technique for placing the composition in the cardiac infarct tissue may be employed in accordance with the present invention. However, minimally invasive techniques will be preferred from both the practitioner's and the patient's perspective, in contrast with existing mechanical devices for limiting infarct expansion (such as the Acorn Cardiovascular or Paracor Medical heart mesh devices). In one embodiment, the composition is placed within the tissue via injection, and such injection may be made directly into the cardiac infarct tissue, into a region of tissue containing such infarct, or into tissue adjacent to or partially or completely surrounding the infarct; the phrases "in/into the infarct", "in/into the tissue", and "within the infarct/tissue" are intended to encompass any of these options. The introduction of the composition may occur at a single location in the infarct tissue, or may occur at multiple locations in the tissue. Depending on such factors as the type of composition used, the patient, the size of the infarct, and other factors, the total quantity of composition placed in the infarct tissue can vary from about 0.25 mL to about 25 mL.

When placed into cardiac infarct tissue in the described quantity, the instant compositions can effect an improvement in at least one hemodynamic parameter following myocardial infarction or other adverse event that causes cardiac tissue damage. As used herein, the term "hemodynamic parameter" refers to properties relating to the flow of blood and the performance of the cardiovascular system in connection therewith, including those pertaining to blood pressure, blood volume, and muscle, vascular, and neuronal function, among other factors, especially when measured with respect to the heart. "Hemodynamic parameters" include other properties and factors related to blood flow as will be readily appreciated by those skilled in the art. Exemplary hemodynamic parameters include, but are not limited to, heart rate, systolic arterial blood pressure, diastolic blood pressure, left ventricular end diastolic pressure, pulmonary capillary wedge pressure, central venous pressure, cardiac output, global ejection fraction, regional ejection fraction, end systolic elastance, diastolic elastance, afterload, preload, stoke volume, or preload recruitable stroke work. The present methods may provide improvement of hemodynamic parameters over the short term, improvement over the long term, or cause "improvement" to the extent that they reduce the degree of deterioration with respect to the parameters. In preferred embodiments, the instant methods can effect an improvement in two or more hemodynamic parameters.

When used in accordance with the instant methods, the instant compositions can reduce the likelihood of cardiac remodeling following myocardial infarction or other adverse event that causes cardiac tissue damage. The likelihood of cardiac remodeling can be affected through the improvement of one or more cardiac volume parameters. As used herein, "cardiac volume parameters" refer to physical measurements of heart tissue volume. Exemplary cardiac volume parameters can include, but are not limited to, global end diastolic or systolic volume, regional end diastolic or systolic volume, or segmental end diastolic or systolic volume. Regional can comprise one or more of apical, mid-ventricular, and basal. Segmental can comprise one or more of apical anterior, apical septal, apical inferior, apical lateral, and apical cap. In view of the American Society of Echocardiography seventeen-segment left ventricle model, and the knowledge of those skilled in the art, other cardiac volume parameters will be readily appreciated. In accordance with the present invention, the one or more cardiac volume parameters may be improved during part or substantially all of the end diastolic phase of the cardiac cycle, during substantially all of the end systolic phase of the cardiac cycle, or both. See, e.g., FIGS. 4-6. In addition to increasing regional wall thickness, the disclosed methods can also influence regional and/or global material properties. For example, treatment in accordance with the present methods not only increases stiffness of the portions of the infarct tissue that has been contacted with the disclosed materials, but also prevents loss of stiffness in the portions of the infarct that have not been directly contacted with the materials. See, e.g., FIG. 7 & Example 3, infra.

The present methods may be employed at any time following myocardial infarction, the classical symptoms of which may include one or more of chest pain, shortness of breath, nausea, vomiting, palpitations, sweating, and anxiety, among other symptoms. As readily appreciated by those skilled in the art, directed detection techniques may also be employed to assess whether a myocardial infarction has occurred, such as, for example, computed tomography (CT), nuclear magnetic resonance (NMR), echocardiography, cardiovascular magnetic resonance, electrocardiogram (ECG), serum troponin levels, or other techniques. The composition of the present invention may be placed in the cardiac infarct tissue as little as less than one hour following myocardial infarction, or can be placed in the cardiac infarct tissue 1-2 hours, several hours, a day, several days, a week, or as much as a month or more following myocardial infarction. The composition may be placed in the infarct tissue in a single session, or in multiple sessions that are spaced apart by seconds, minutes, hours, or days, in uniform or unequal intervals, as desired.

The commercial potential of the instant therapeutic approach is greatly strengthened by the recent development of catheter-based technologies for the precise regional delivery of materials into the myocardium without the need for surgery. These technologies have been developed by several companies with the intent of delivering cell based and gene based therapies to the myocardium. As disclosed herein, such technologies can be applied to the entirely novel use of particulate materials for the regulation of infarct expansion, improvement of one or more hemodynamic parameters, or both. Other means of placing the composition comprising a particulate, biologically, compatible, inorganic material may also be used. Three approaches may be envisioned as non-limiting choices for delivery of the instant compositions: epicardial injection, endocardial injection, and intracoronary injection. Epicardial delivery, which involves direct injection with a needle and syringe through a standard surgical incision to expose the heart, may be thoracoscopically or otherwise endoscopically assisted, for example, using standard or modified mediastinoscopes or bronchoscopes. Robotically assisted and/or guided approaches to direct injection may also be employed. Catheter based endocardial injection from inside the ventricular cavity may make use of presently commercially available devices. See, e.g., Sherman W, et al., *Catheter-based delivery of cells to the heart, Nat Clin Pract Cardiovasc Med.* 2006 March; 3 Suppl 1:S57-64. Intracoronary injection could involve catheter-base direct injection into or through a coronary artery or vein. For example, a catheter may be guided to the site of the infarct using the venous system, after which a needle may be used to penetrate the guide vein wall and inject the current compositions into the myocardium. See id.

Also provided are kits comprising a composition comprising a particulate, biologically compatible, inorganic material and an injection tool capable of delivering the filler material to a region comprising an infarct or a portion thereof within a living patient. As discussed previously, the particulate material can be any substance that attenuates heart remodeling by thickening the infarct region. The preceding discussion in connection with the inventive methods should be referenced with regard to other characteristics of the composition and the particulate, biologically compatible, inorganic material. In the instant kits, the composition may be provided in premeasured aliquots, the volume of each aliquot corresponding a single use of a kit. Multiple compositions can be provided, as can be mixtures of one or more compositions. The injection tool can comprise a catheter system. Delivery systems as previously described and as understood by those skilled in the art are contemplated for inclusion within the present kits. The injection tool or any portion thereof may be resusable, or suitable for a single use only. Instructions for use of the instant kits may also be provided.

EXAMPLES

Experiments were conducted to determine whether intramyocardial injection of an acellular dermal filler material currently available for cosmetic facial procedures can reduce infarct expansion, limit global remodeling and improve contractile function within non-ischemic territories when injected early after myocardial infarction (MI). The material used in these studies comprised viscous fluid that can be delivered by percutaneous catheter-based methods that are currently being developed to support myocardial cell and gene based therapeutic strategies. See, e.g., Sherman W, et al., *Catheter-based delivery of cells to the heart, Nat Clin Pract Cardiovasc Med.* 2006 March; 3 Suppl 1:S57-64.

Example 1

Experimental Materials and Methods

Biocompatible Dermal Filler.

Radiesse® (Bioform Medical Inc, San Mateo, Calif.) is a viscous (gel-like consistency) biocompatible dermal and soft tissue filler of calcium hydoxyapatite microspheres suspended in an aqueous gel carrier of water, glycerin and carboxymethylcellulose. Once injected, fibroblasts grow on the surface of the microspheres, replacing the carrier over time. Shimizu S I. *Subcutaneous tissue response in rats to injection of fine particles of synthetic hydroxyapatite ceramic. Biomed Res* 1988; 9:95-111. Radiesse® has been studied in diverse applications including radiopaque tumor marking, bladder neck augmentation, vocal cord injection and cosmetic facial-volume augmentation. Tzikas T L. *Evaluation of the Radiance FN soft tissue filler for facial soft tissue augmentation. Arch Facial Plast Surg.* 2004; 6:234-239; Kanchwala S K et al., *Reliable Soft Tissue Augmentation: A Clinical Comparison of Injectable Soft-Tissue Fillers for Facial-Volume Augmentation. Annals of Plastic Surgery* 2005; 55: 30-35; Hobar P C et al., *Porous hydroxyapatite granules for alloplastic enhancement of the facial region. Clin Plast Surg* 2000; 27:557-569; Havlik R J. *Hydroxyapatite. Plast Reconstr Surg* 2002; 110:1176-1179. Because calcium hydroxyapatite is the major mineral component of bone and both of its component ions are metabolized in the body, neither intraluminal introduction nor systemic absorption of the minerals would be expected to cause systemic toxicity. See Drobeck H P et al., *Histologic observation of soft tissue responses to implanted, multifaceted particles and discs of hydroxylapatite. J Oral Maxillofac Surg* 1984; 42(3):143-149.

Surgical Protocol.

The study protocol was reviewed and approved by the University of Pennsylvania School of Medicine Institutional Animal Care and Use Committee (IACUC). In compliance with guidelines for humane care (National Institutes of Health Publication No. 85-23, revised 1996), 15 adult male sheep (35-40 kg) were pretreated with buprenorphine (2 mcg/kg) and then induced with sodium thiopental (10-15 mg/kg IV), intubated and anesthetized with isofluorane (1.5-2.0%) and oxygen. The electrocardiogram, arterial blood pressure, LV pressure and pulmonary artery pressure were monitored throughout the procedure. A left thoracotomy was performed and baseline echocardiographic data were acquired. Suture ligatures were placed around the left anterior descending artery (LAD) and its second diagonal branch 40% of the distance from the apex to the base of the heart. Occlusion of these arteries at these locations reproducibly results in a moderately sized infarction involving slightly more than 20% of the left ventricular mass at the anteroapex. Markovitz L J et al. *Large animal model of left ventricular aneurysm. Ann Thorac Surg* 1989; 48:838-845. Echocardiographic image acquisition was then repeated thirty minutes after infarction.

Forty-five minutes after infarction, 1.3 mL of Radiesse® was injected at 25 uniformly spaced points within the ischemic territory, in each case to a depth of approximately 2 mm. Echocardiographic image acquisition was again repeated 15 minutes after injection.

Echocardiographic Protocol.

Epicardial real-time three-dimensional echocardiography was performed through a left thoracotomy immediately prior to MI, 30 minutes after MI and 15 minutes after gel injection in all subjects. In each case, ECG gated full-volume images were acquired by a single, experienced operator using a Sonos 7500 (Philips Medical Systems, Andover, Mass.) platform equipped with a 2-4 MHz phased array probe and an X4 matrix-array handheld transducer. Each full volume data sets was exported to a dedicated workstation (Dell Optiplex GX 270, Dell Inc., Round Rock, Tex.) for image manipulation and analysis. Heart rate (HR), arterial blood pressure (ABP), left ventricular pressure (LVP), pulmonary artery pressure (PAP), pulmonary capillary wedge pressure (PCWP), central venous pressure (CVP) and cardiac output (CO) were recorded at the time of echocardiographic data acquisition.

Image Analysis.

Image analysis was performed using QLab 3D Advanced Quantification Software (Philips Medical Systems, Andover, Mass.). For each data set, left ventricular endocardial contours were manually traced in both end diastolic and end systolic frames. The endocardial contours of the remaining frames were traced in sequence by means of automated contour detection. The resulting four dimensional LV model was then automatically segmented in accordance with the American Society of Echocardiography (ASE) 17-segment model. The global and segmental volume-time curves were then exported as Excel CSV (Microsoft, Redmond, Wash.) files for further analysis.

Data Analysis.

Global end diastolic and end systolic volumes (EDV, ESV), which were defined as the maximum and minimum LV cavity volumes, were extracted from the global volume-time curve for each data set at each observation interval. Global ejection fraction (EF) was defined as $\{[EDV-ESV]/EDV\}\times 100\%$.

For each data set, the cardiac cycle was normalized to a length of 800 msec (systole=500 msec, diastole=300 msec), where end diastole and end systole were defined as the time points corresponding to the maximum and minimum global LV volumes, respectively. A shape preserving interpolant was then fit to the time normalized global time-volume curve and to each of the 17 time normalized segmental volume-time curves within a given data set after which interpolated volumes were extracted at 1 msec intervals for the global curve and for each segmental curve. For each data set, interpolated volumes from segments 1-6 were merged into a single basal regional volume-time curve. Interpolated volumes from segments 7-12 were merged into a single mid-ventricular regional volume-time curve while those from segments 13-17 were merged into a single apical regional volume-time curve. Basal, mid-ventricular and apical regional EDV, ESV and EF were then calculated for each data set from these regional volume-time curves.

In order to clearly characterize the effect of Radiesse® injection on infarct expansion EDV, ESV and EF were calculated for each of the five segments comprising the apical region-apical anterior (segment 13), apical septal (segment 14), apical inferior (segment 15), apical lateral (segment 16) and the apical cap (segment 17). In all animals segment 17 was contained entirely within the infarct while the other segments (13-16) that contributed to the apical region contained both infarcted and perfused myocardium to a variable degree. Fifteen subject hybrid volume-time curves were constructed for each of the five apical segments at baseline, following infarction and following injection.

Statistical comparison between individual values at baseline, 30 minutes after infarction and 15 minutes after gel injection were made with a student's t-test for paired observations. All statistical analysis was performed using SPSS (Statistical Package for the Social Sciences, SPSS Inc, Chicago, Ill.). The level of significance selected for all variables was $p<0.05$. P-values were computed with reference to baseline values following infarction and with reference to post-infarction values following injection. All data are reported as mean±SEM.

Example 2

Experimental Results

Hemodynamics and Remodeling.

In the control group global LV ESV increased from 23.5±2.2 ml at baseline to 60.7±3.6 ml 4 weeks after infarction. In the dermal filler treated group, ESV increased from 23.6±1.6 ml at baseline to 47.0±3.9 ml 4 weeks after infarction ($p<0.05$ vs. control). Global LV EDV increased from 48.1±3.7 ml at baseline to 85.8±3.7 ml 4 weeks after infarction in the control group. In the dermal filler treated group, LV EDV increased from 47.1±3.0 ml at baseline to 74.9±2.9 ml 4 weeks after infarction ($p=0.05$ vs. control). EF 4 weeks after MI in the dermal filler treated group (37.3±2.7%) was significantly higher than in the control group (29.5±1.6%, $p=0.05$). Remodeling and hemodynamic data are presented in Table 2, below, in which data are presented as mean±SEM for each observation interval. *=$p<0.05$ vs. Pre-myocardial infarction; †=$p<0.05$ vs. Control. Abbreviations include: Myocardial Infarction (MI) Left Ventricular End Systolic Volume (LVESV), Left Ventricular End Diastolic Volume (LVEDV), Left Ventricular End Diastolic Pressure (LVEDP), Central Venous Pressure (CVP).

TABLE 2

| | Pre-MI | | Post-MI | | Post-Injection | | 4 weeks Post-MI | |
|---|---|---|---|---|---|---|---|---|
| | Control | Dermal Filler (Radiesse ®) | Control | Dermal Filler (Radiesse ®) | Control | Dermal Filler (Radiesse ®) | Control | Dermal Filler (Radiesse ®) |
| LVESV (mL) | 23.5 ± 2.2 | 23.7 ± 1.6 | 38.9 ± 2.4* | 39.9 ± 1.8* | 39.3 ± 2.6* | 33.4 ± 1.7*† | 61.2 ± 3.6* | 44.5 ± 3.9*† |
| LVEDV (mL) | 48.1 ± 3.7 | 47.1 ± 3.0 | 66.1 ± 3.4* | 64.8 ± 3.0* | 65.9 ± 3.5* | 58.6 ± 2.8* | 85.7 ± 3.7* | 70.7 ± 3.9* |
| Ejection Fraction (%) | 51.7 ± 1.7 | 49.8 ± 1.5 | 41.0 ± 1.9* | 38.2 ± 1.1* | 40.3 ± 1.9* | 42.7 ± 1.8* | 29.5 ± 1.6* | 37.3 ± 1.7*† |
| Cardiac Output (L/min) | 4.6 ± 0.2 | 4.9 ± 0.4 | 2.7 ± 0.5* | 2.6 ± 0.5* | 2.6 ± 0.4* | 3.1 ± 0.2* | 2.8 ± 0.3* | 3.9 ± 0.3*† |
| LVEDP (mmHg) | 5 ± 2 | 4 ± 1.5 | 19 ± 6 | 20 ± 7 | 19 ± 6 | 16 ± 5 | 12 ± 4 | 9 ± 3 |
| CVP (mmHg) | 13 ± 3 | 12 ± 2 | 14 ± 2 | 13 ± 4 | 15 ± 3 | 12 ± 2 | 11 ± 2 | 10 ± 1 |

Global Remodeling.

FIG. 1A provides left ventricular global end diastolic volumes (EDV) and end systolic volumes (ESV) at baseline, 30 minutes after infarction, and 15 minutes after injection with filler material. FIG. 1B depicts corresponding ejection fraction data. Global EDV and ESV increased from 47.1±3.0 mL and 23.7±1.6 mL at baseline to 64.8±3.0 mL ($p<0.001$) and 39.9±1.8 ml ($p<0.001$) after infarction and then decreased to 58.6±2.8 mL ($p=0.001$) and 33.4±1.7 mL ($p<0.001$) after injection (FIG. 1A). EF decreased from 49.8±1.5% at baseline to 38.2±1.1% after infarction ($p<0.001$) and then increased to 42.7±1.8% after injection ($p<0.05$) (FIG. 1B).

Regional Remodeling.

Figure 2:
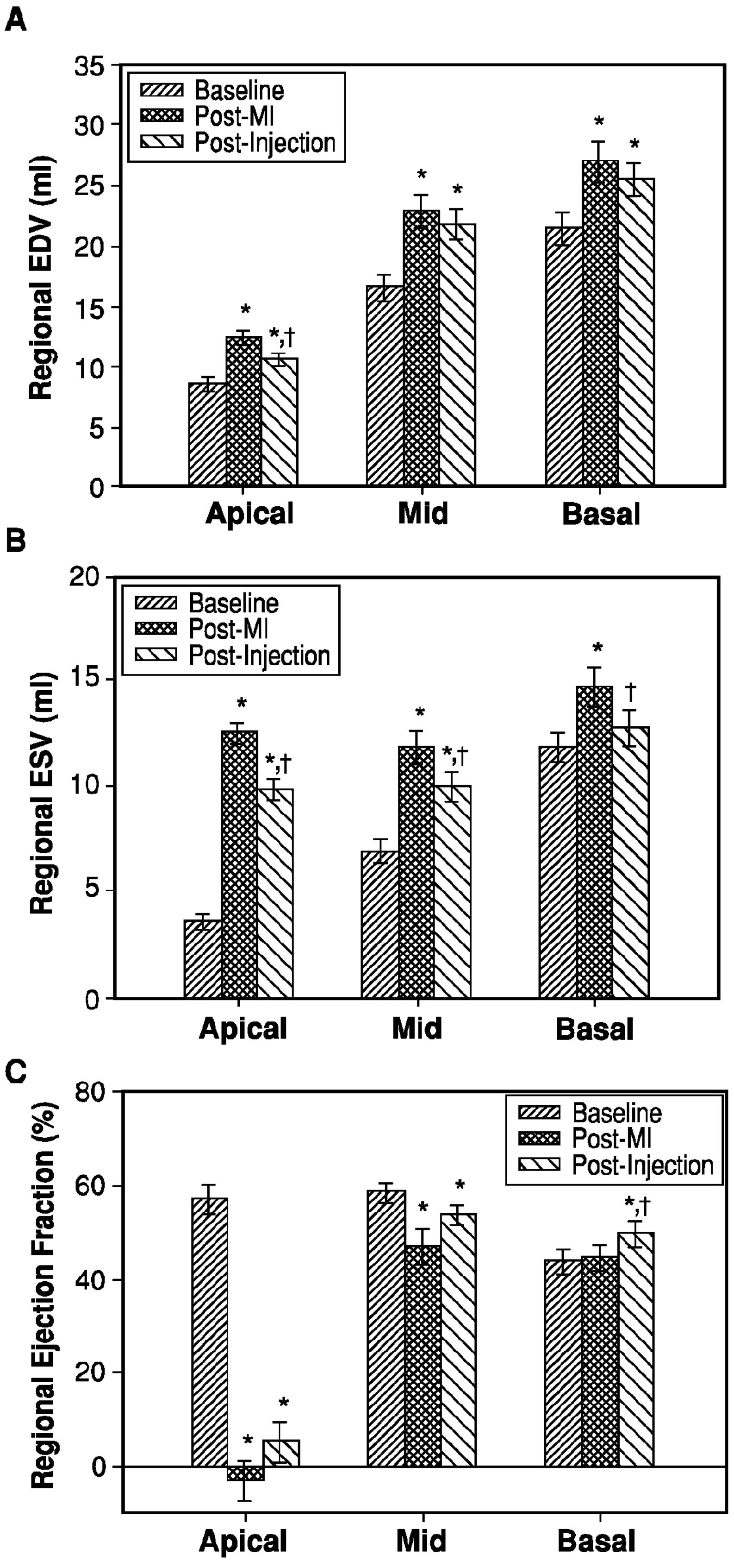
FIG. 2 shows regional end diastolic volume (EDV, part A), end systolic volume (ESV, part B) and ejection fraction (part C) for each of the three left ventricular regions, presented at baseline, 30 minutes after infarction and 15 minutes after injection.

FIGS. 2A-C depict data for regional end diastolic volume (EDV, part A), end systolic volume (ESV, part B) and ejection fraction (part C) for each of the three left ventricular regions, presented at baseline, 30 minutes after infarction and 15 minutes after injection. Data are presented as mean±SEM, * indicates $p<0.05$ with respect to the corresponding value at baseline, while † indicates $p<0.05$ with respect to the corresponding value following infarction.

Apical regional EDV and ESV increased from 8.5±0.6 mL and 3.6±0.3 mL respectively at baseline to 12.4±0.6 mL ($p<0.001$) and 12.5±0.5 mL ($p<0.001$) after MI and then decreased to 10.6±0.5 mL ($p<0.05$) and 9.9±0.5 mL ($p<0.001$) after injection while apical regional EF decreased from 57.3±3.1% to −2.8±4.2% ($p<0.001$) and then increased to 5.3±4.3% ($p=0.12$) after injection.

Mid-ventricular EDV and ESV increased from 16.6±1.1 mL and 7.0±0.6 mL respectively at baseline to 22.9±1.4 mL ($p<0.001$) and 11.8±0.8 mL ($p<0.001$) after MI and then decreased to 21.8±1.2 mL ($p>0.05$) and 10.1±0.7 mL ($p<0.05$) after injection, while mid-ventricular EF decreased from 58.5±2.0% to 47.1±4.0% ($p<0.05$) and then increased to 53.7±2.2% ($p=0.11$) after injection.

Basal EDV and ESV increased from 21.5±1.3 mL and 11.8±0.7 mL, respectively, at baseline to 27.0±1.7 mL ($p<0.001$) and 14.7±0.9 mL ($p<0.001$) after MI and then decreased to 25.5±1.3 ($p>0.05$) and 12.8±0.9 ($p<0.05$) after injection, while basal EF increased from 43.9±2.6% to 44.7±2.7% ($p>0.05$) and then to 49.7±2.7% ($p<0.05$).

Apical Segmental Remodeling.

Figure 3:
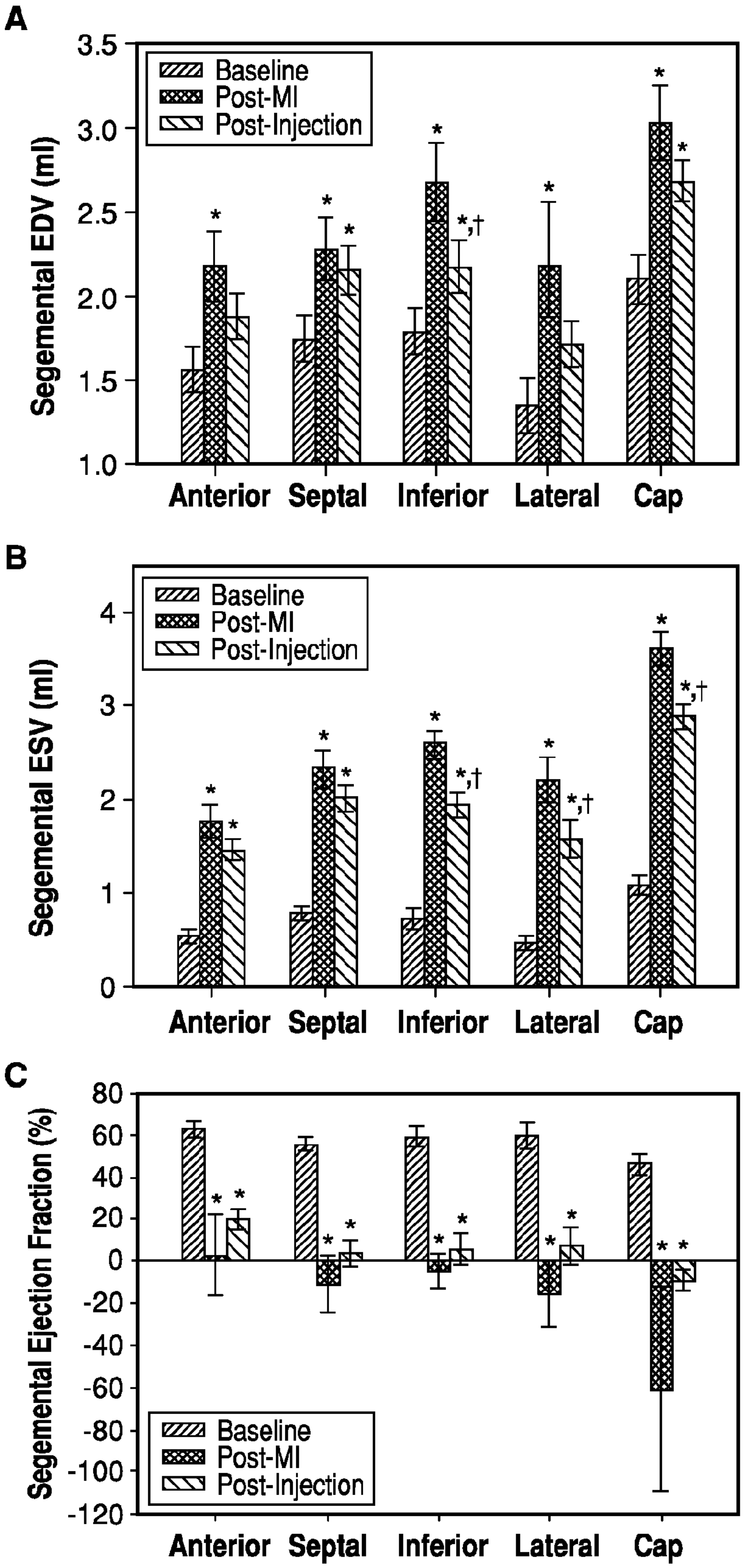
FIG. 3 depicts apical segmental end diastolic volume (EDV, part A), end systolic volume (ESV, part B) and ejection fraction (part C) for each of the five left ventricular segments that comprise the apical region, presented at baseline, 30 minutes after infarction and 15 minutes after injection.

FIGS. 3A-C depict apical segmental end diastolic volume (EDV, part A), end systolic volume (ESV, part B) and ejection fraction (part C) for each of the five left ventricular segments that comprise the apical region, presented at baseline, 30 minutes after infarction and 15 minutes after injection.

Apical anterior EDV and ESV increased from 1.6±0.1 mL and 0.5±0.1 mL respectively at baseline to 2.2±0.2 mL ($p<0.05$) and 1.8±0.2 mL ($p<0.001$) after MI and then decreased to 1.9±0.1 mL ($p=0.14$) and 1.5±0.1 mL ($p=0.13$) after injection while EF decreased from 63.1±4.0% to 2.8±19.3% ($p<0.05$) and then increased to 20.2±4.9% ($p=0.37$). Apical septal EDV and ESV increased from 1.7±0.1 mL and 0.8±0.1 mL respectively at baseline to 2.3±0.2 mL ($p<0.05$) and 2.3±0.2 mL ($p<0.001$) after MI and then decreased to 2.2±0.1 mL ($p=0.56$) and 2.0±0.1 mL ($p=0.11$) after injection while EF decreased from 55.7±3.1% to −11.0±13.4% ($p<0.001$) and then increased to 3.5±6.2% ($p=0.30$). Apical inferior EDV and ESV increased from 1.8±0.1 mL and 0.7±0.1 mL respectively at baseline to 2.7±0.2 mL ($p<0.05$) and 2.6±0.1 mL ($p<0.001$) after MI and then decreased to 2.2±0.2 mL ($p<0.05$) and 2.0±0.1 mL ($p<0.05$) after injection while EF decreased from 59.3±5.1% to −4.6±8.4% ($p<0.001$) and then increased to 5.8±7.6% ($p=0.21$). Apical lateral EDV and ESV increased from 1.3±0.2 mL and 0.5±0.1 mL respectively at baseline to 2.2±0.3 mL ($p<0.05$) and 2.2±0.1 mL ($p<0.001$) after MI and then decreased to 1.7±0.2 mL ($p=0.07$) and 1.8±0.1 mL ($p<0.001$) after injection while EF decreased from 60.0±6.0% to −15.8±15.7% ($p<0.001$) and then increased to 7.0±8.8% ($p=0.123$). Apical cap (segment 17) EDV and ESV increased from 2.1±0.2 mL and 1.1±0.1 mL respectively at baseline to 3.0±0.2 mL ($p<0.001$) and 3.6±0.2 mL ($p<0.001$) after MI and then decreased to 2.7±0.1 mL ($p<0.08$) and 2.8±0.1 mL ($p<0.001$) after gel injection while EF decreased from 46.5±4.7% to −60.8±48.8% ($p<0.05$) and then increased to −9.2±4.8% ($p=0.31$).

Volume-Time Plots.

Figure 4:
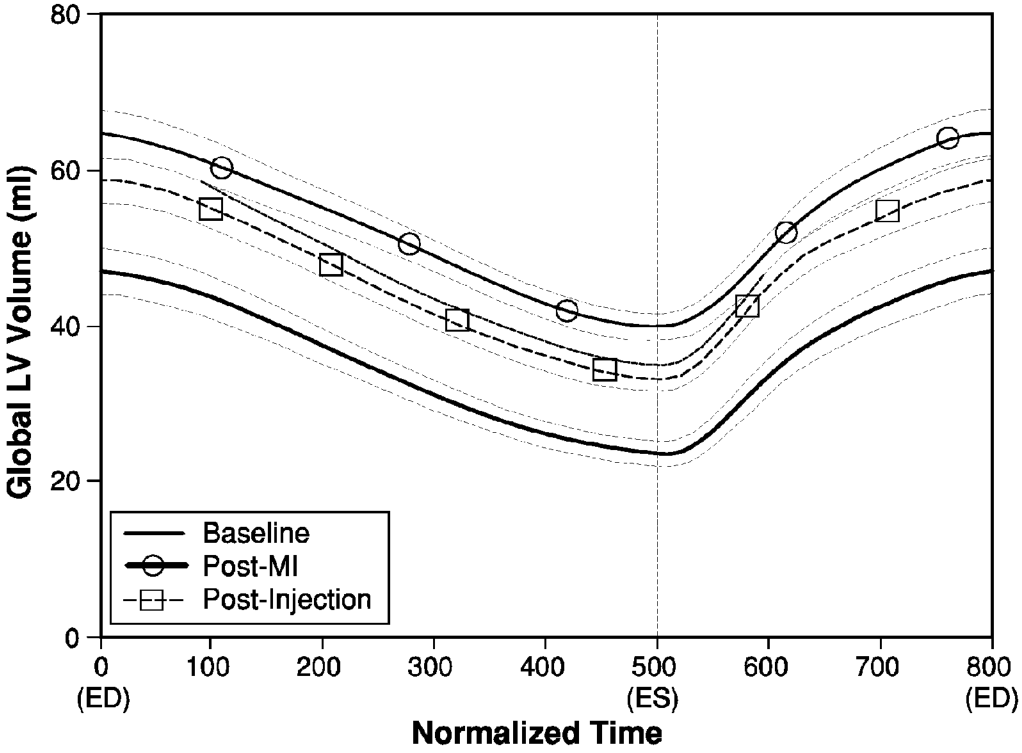
FIG. 4 shows global left ventricular (LV) volume plotted as a function of normalized time at baseline, 30 minutes after infarction and 15 minutes after injection for a 15-subject cohort on a common axis.

In FIG. 4, global LV volume is plotted as function of normalized time for each of baseline, 30 minutes after infarction and 15 minutes after injection for a 15-subject cohort on a common axis. Data is presented as mean (solid line)±SEM (dotted line). End diastole (ED) occurs at 0 msec and 800 msec, while end systole (ES) occurs at 500 msec.

A significant increase in LV volume was observed at all phases of the cardiac cycle after infarction and the subsequent reduction in LV volumes after injection of the dermal filler.

Figure 5:
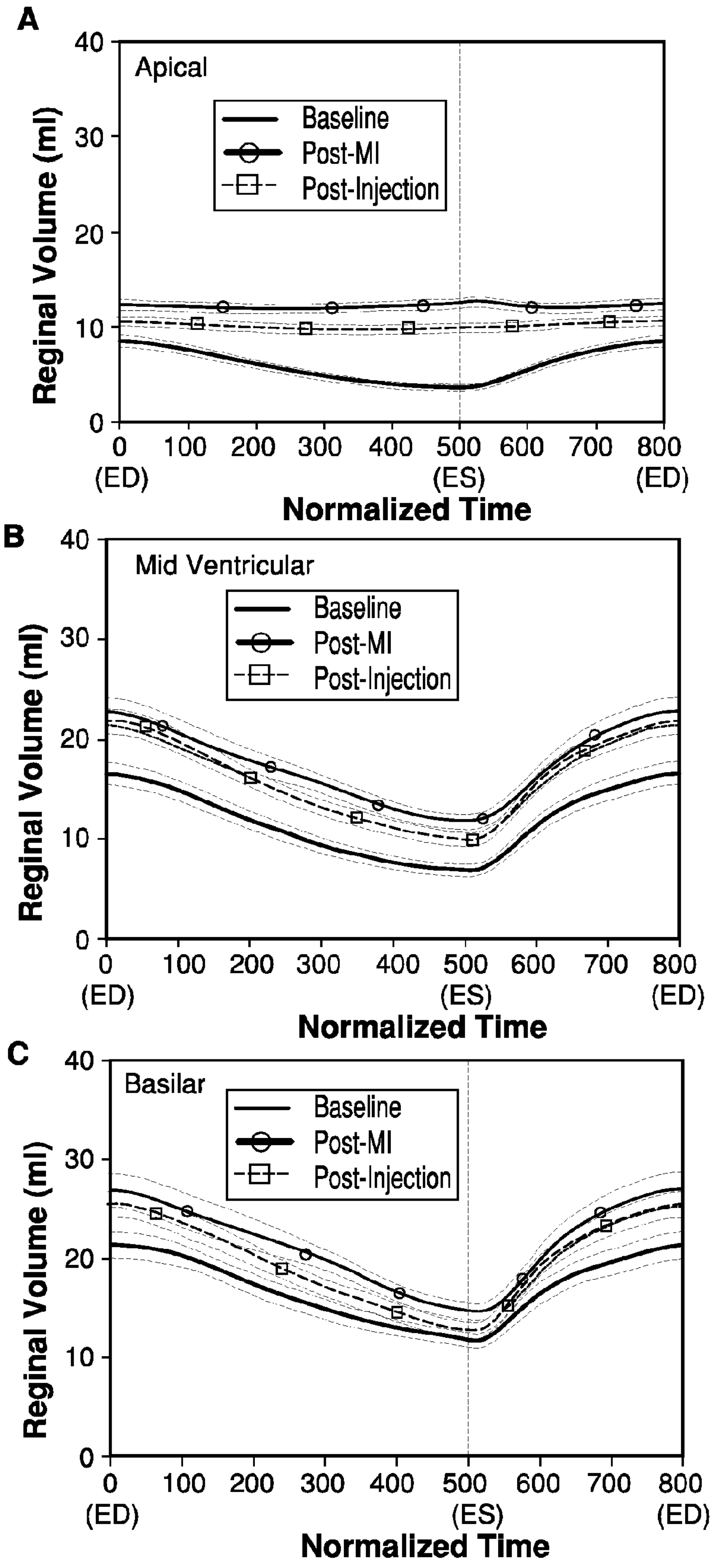
FIG. 5 provides plots of apical (A), mid-ventricular (B) and basal (C) regional volumes as functions of normalized time at baseline, 30 minutes after infarction and 15 minutes after gel injection for the 15 subject cohort on common axes.
Figure 6:
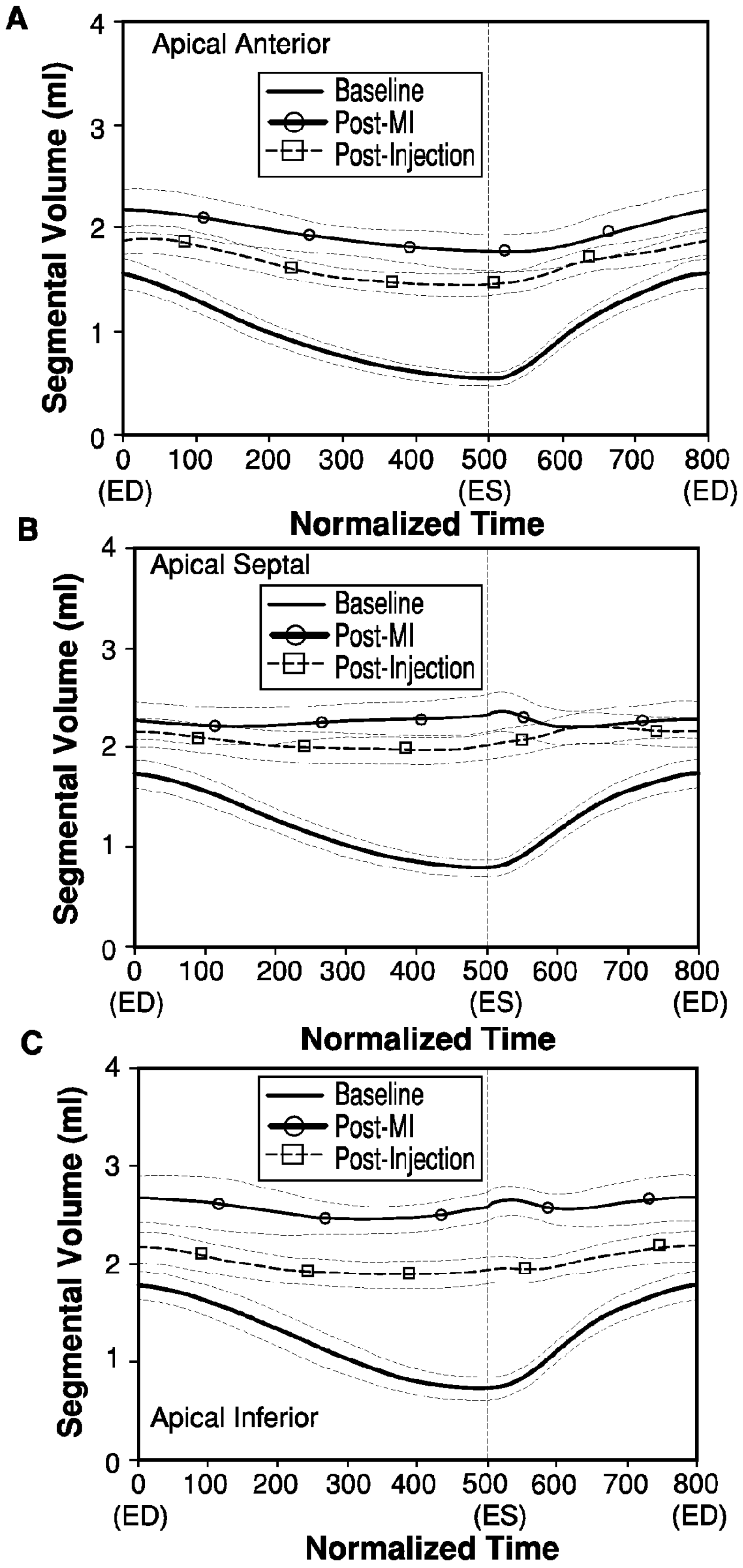
FIG. 6 provides plots of apical anterior (A), apical septal (B), apical inferior (C), apical lateral (D) and apical cap (E) segmental volumes as functions of normalized time at baseline, 30 minutes after infarction and 15 minutes after gel injection for the 15-subject cohort on common axes.
Figure 7:
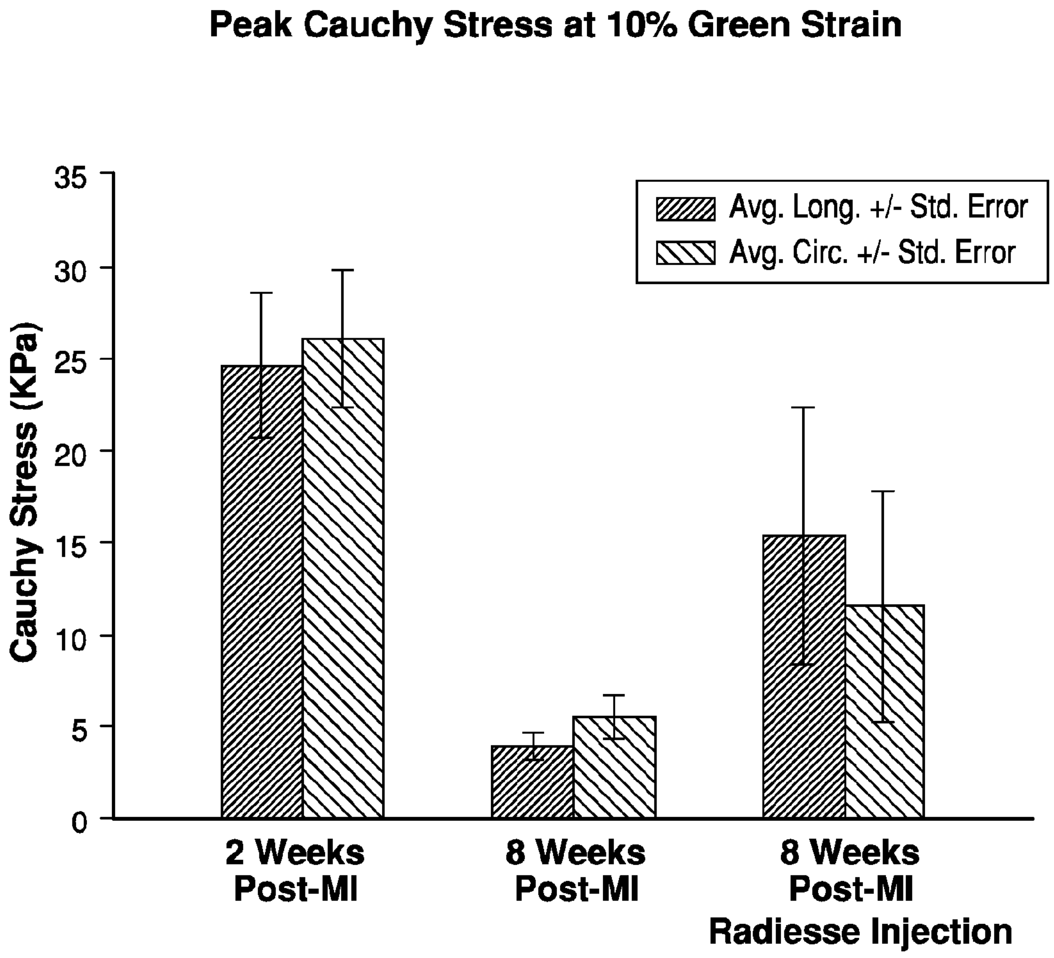
FIG. 7 depicts infarct stiffness as assessed by biaxial stretching (Cauchy Stress) at two and eight weeks after infarction in untreated controls and animals that received treatment immediately after infarction.
Figure 8:
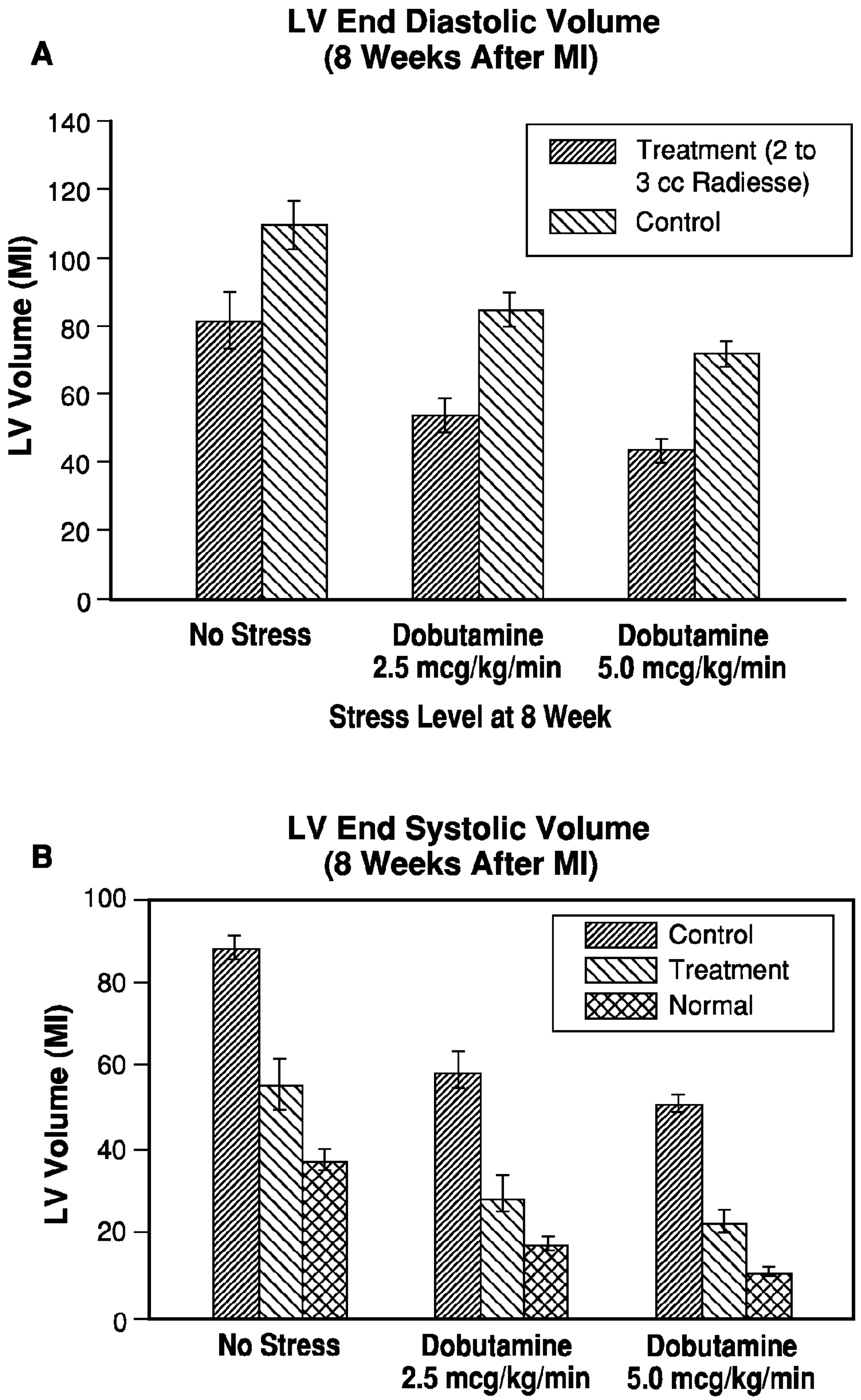
FIGS. 8A and 8B provide plots of LV end diastolic and systolic volume, respectively, determined by stress echocardiography at eight weeks after anteroapical myocardial infarction in sheep.

FIG. 5 provides plots of apical (A), mid-ventricular (B) and basal (C) regional volumes as functions of normalized time at baseline, 30 minutes after infarction and 15 minutes after gel injection for the 15 subject cohort on common axes. FIG. 6 provides plots of apical anterior (A), apical septal (B), apical inferior (C), apical lateral (D) and apical cap (E) segmental volumes as functions of normalized time at baseline, 30 minutes after infarction and 15 minutes after gel injection for the 15-subject cohort on common axes. In both FIGS. 5 and 6, data is presented as mean (solid line)±SEM (dotted line), and end diastole occurs at 0 msec and 800 msec, while end systole occurs at 500 msec. Regional volumes increased throughout the cardiac cycle for each of the three defined regions following infarction, while paradoxical systolic bulging only occurred within the apical region and was most pronounced in the apical cap segment. Regional volumes decreased throughout the cardiac cycle for each of the three defined regions following gel injection. Additionally, paradoxical systolic bulging is absent within the apical cap segment following injection indicating a transition from apical dyskinesia to akinesia.

All animals in the present study were subjected to a moderately sized transmural anteroapical MI which resulted in immediate expansion of the infarct region, global LV dilatation and a decrease in global LV function. A regional analysis of remodeling using three dimensional echocardiography demonstrated that all regions (apical, midventricular and basilar) contributed to the global increase in ventricular volume. The regional EF of the apex became negative after infarction, consistent with systolic dyskinesia. The EF of the normally perfused midventricular region was also significantly decreased relative to baseline while the basilar regional EF remained unchanged after infarction. These global and regional responses to MI are similar to those documented previously by the present inventors using this infarct model and a combination of sonomicrometry and two dimensional echocardiography. Jackson B M et al., *Extension of borderzone myocardium in postinfarction dilated cardiomyopathy. J Am Coll Cardiol* 2002; 40:1160-1167.

Injection of 1.3 mL of Radiesse® into the infarct region converted the apical wall motion from dyskinetic to akinetic and resulted in significant decreases in global, regional and segmental LV volumes. Injection of the filler material was also associated with a significant improvement global EF. The improvement in global EF was due to improved regional EF in both the midventricular and basilar portion of the ventricle.

Example 3

Infarct Stiffness

The effect of injection of volume-increasing material on infarct stretching was assessed using a biaxial stretching device. The biaxial stretching technique is described in detail in Gupta, et al., *Changes in passive mechanical stiffness of myocardial tissue with aneurysm formation. Circulation* 1999; 85: 2315-2326. Infarct tissue was harvested from four untreated animals two weeks after infarction and another four untreated animals eight weeks after infarction and stretched to 1.1 times its initial size (10% strain). A similar test was performed on four animals that survived eight weeks after 2-3 mL of volume-increasing material had been injected into the infarct region immediately after coronary ligation. The more force or stress required to stretch the material 10% is an indicator of tissue stiffness. Results are summarized in FIG. 7. Briefly, in untreated animals the infarct was stiffest two weeks after infarction then decreased significantly by eight weeks after infarction. Radiesse® injection significantly increased infarct stiffness relative to untreated controls eight weeks after infarction.

Example 4

Infarct Stiffness as a Function of Increasing Dose of Filler Material

Figure 12A:
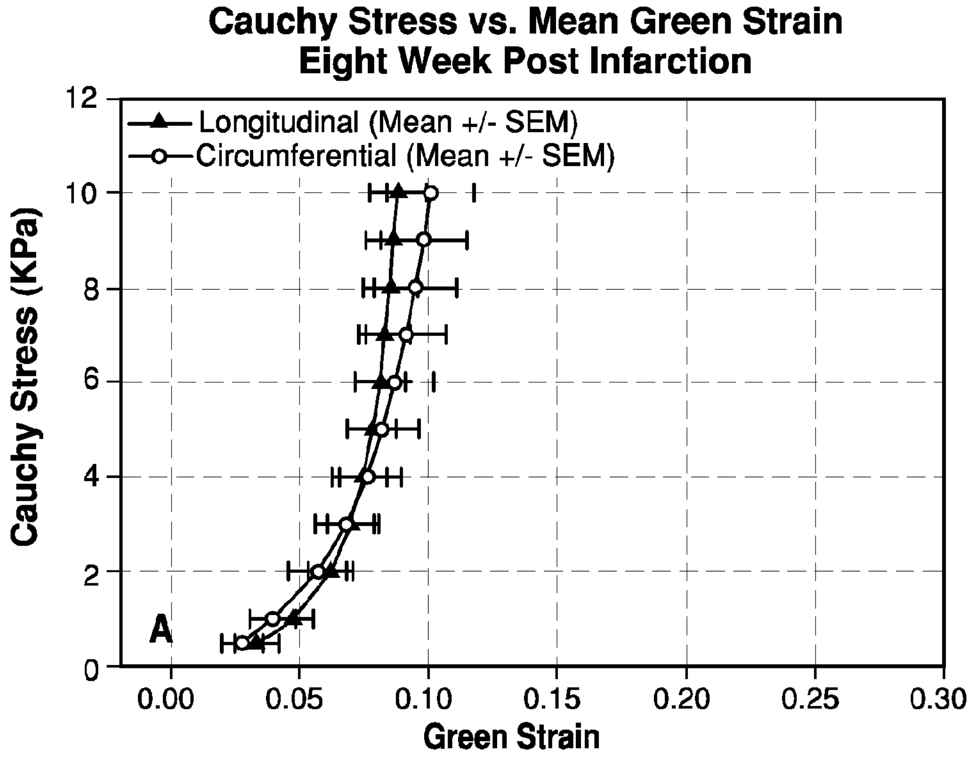
FIGS. 12A-C provide biaxial stress-strain curves for (A) untreated sheep apical infarct tissue, (B) infarct tissue into which 1 mL of volume-increasing material had been injected after infarction, and (C) infarct tissue into which 3 mL of volume-increasing material had been injected after infarction.
Figure 12B:
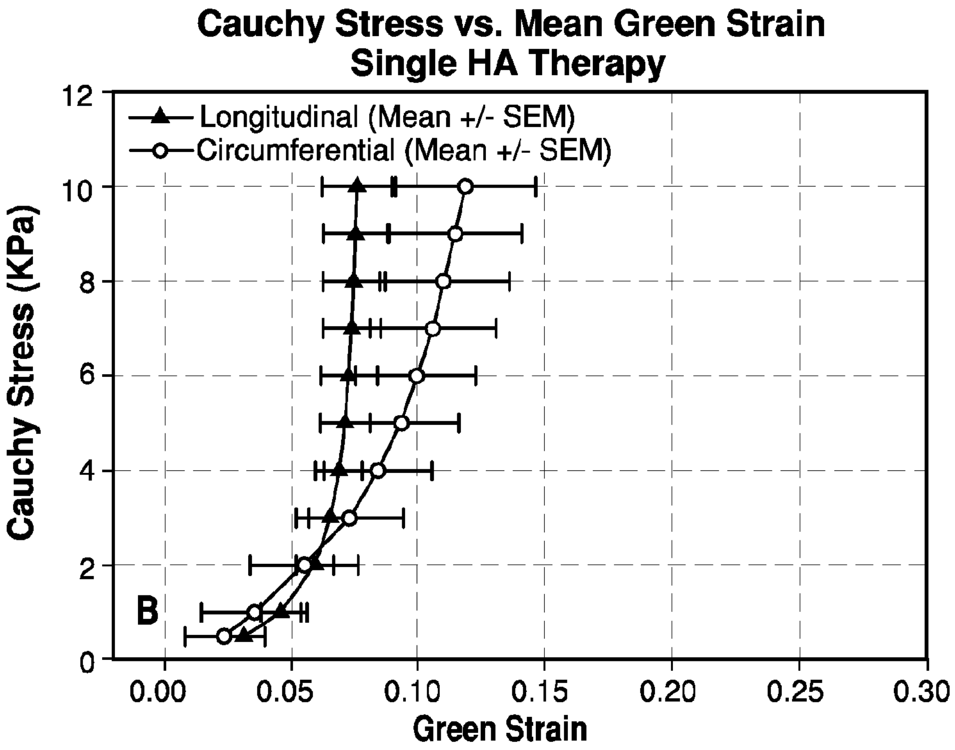
Figure 12C:
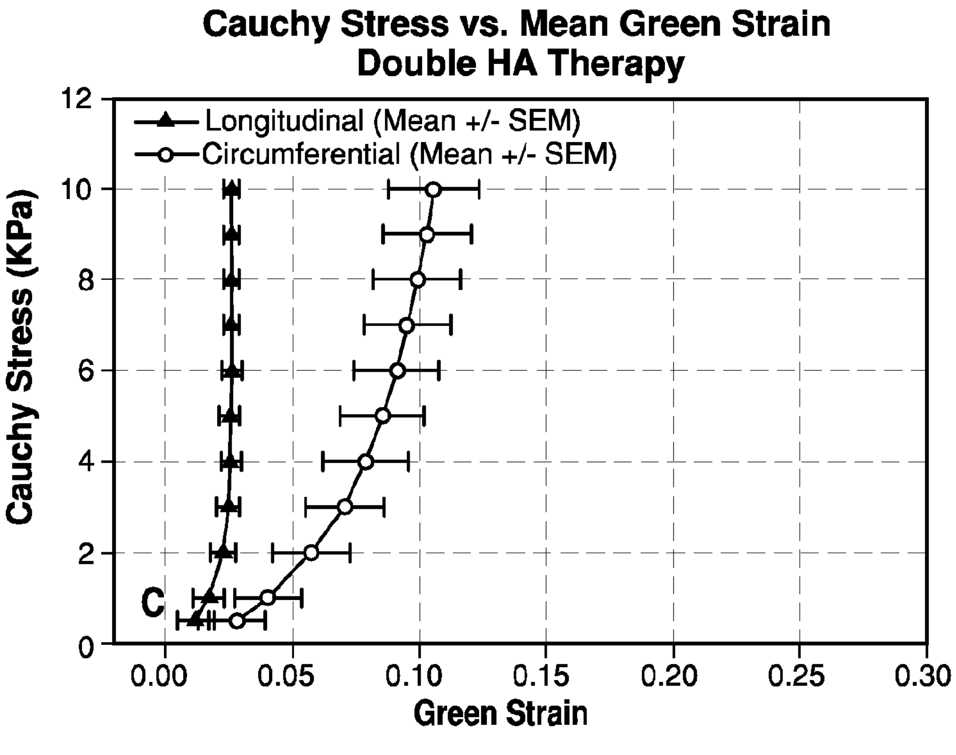

The effect of increasing doses of volume-increasing material on infarct stretching was also assessed using a biaxial stretching device. As indicated above, the biaxial stretching technique is described in detail in Gupta, et al. FIG. 12 depicts biaxial stress-strain curves for untreated sheep apical infarct tissue 8 weeks after myocardial infarct (FIG. 12A), tissue 8 weeks after myocardial infarct that had been treated with 1 mL of Radiesse® volume-increasing material three hours after infarction (FIG. 12B), and infarct tissue 8 weeks after myocardial infarct that had been treated with 3 mL of Radiesse® three hours after infarction (FIG. 12C). A progressive increase in infarct longitudinal stiffness was associated with increasing dose of volume-increasing material (n=7 animals for all groups).

Example 5

Chronic Effect of Treatment on LV Remodeling and Function

This study was performed to assess the more long-term effect of injection of volume-increasing material on LV remodeling and function. The study protocol was reviewed and approved by the University of Pennsylvania School of Medicine Institutional Animal Care and Use Committee (IACUC). In compliance with guidelines for humane care (National Institutes of Health Publication No. 85-23, revised 1996), 20 adult male sheep (40-45 kg) were pretreated with buprenorphine (2 mcg/kg) and then induced with sodium thiopental (10-15 mg/kg IV), intubated and anesthetized with isoflurane (1.5-2.0%) and oxygen. The electrocardiogram, arterial blood pressure, LV pressure and pulmonary artery pressure were monitored throughout the procedure. A left thoracotomy was performed and baseline echocardiographic data were acquired. Suture ligatures were placed around the left anterior descending artery (LAD) and its second diagonal branch 40% of the distance from the apex to the base of the heart. Occlusion of these arteries at these locations reproducibly results in a moderately sized infarction involving slightly more than 20% of the left ventricular mass at the anteroapex. Markovitz L J et al. *Large animal model of left ventricular aneurysm. Ann Thorac Surg* 1989; 48:838-845. Echocardiographic image acquisition was then repeated thirty minutes after infarction.

Seven animals were randomly selected for treatment. In these animals at 45 minutes after infarction, 2-3 mL of Radiesse® was injected at 25 uniformly spaced points within the infarct region, in each case to a depth of approximately 2 mm. The remaining 13 animals served as untreated controls Echocardiographic image acquisition was again repeated 15 minutes after injection.

Transdiaphragmatic real-time three-dimensional echocardiography was then performed 8 weeks after infarction to assess LV remodeling (volume at end diastole and end systole) and ejection fraction. In each case, ECG gated full-volume images were acquired by a single, experienced operator using a Sonos 7500 (Philips Medical Systems, Andover, Mass.) platform equipped with a 2-4 MHz phased array probe and an X4 matrix-array handheld transducer. Each full volume data sets was exported to a dedicated workstation (Dell Optiplex GX 270, Dell Inc., Round Rock, Tex.) for image manipulation and analysis. Heart rate (HR), arterial blood pressure (ABP), left ventricular pressure (LVP), pulmonary artery pressure (PAP), pulmonary capillary wedge pressure (PCWP), central venous pressure (CVP) and cardiac output (CO) were recorded at the time of echocardiographic data acquisition. At the 8 week post-infarction study echocardiographic and hemodynamic data were recorded at three stress levels: no inotropic stimulation; infusion of 2.5 mcg/kg/min dobutamine; infusion of 5.0 mcg/kg/min dobutamine. After the 8 week echocardiographic studies the heart was excised and the wall thickness of the myocardium was measured at the following positions: apical aspect of the infarct; basilar aspect of the infarct; uninfarcted borderzone myocardium; infarcted remote myocardium.

Global end diastolic and end systolic volumes (EDV, ESV), which were defined as the maximum and minimum LV cavity volumes, were extracted from the global volume-time curve for each data set at each observation interval. Global ejection fraction (EF) was defined as $\{[EDV-ESV]/EDV\}\times 100\%$. Statistical comparison between individual values at baseline, 30 minutes after infarction and 15 minutes after gel injection were made with a student's t-test for paired observations.

Statistical comparison between the treatment and control groups were made with a student's t-test for unpaired observations. All statistical analysis was performed using SPSS (Statistical Package for the Social Sciences, SPSS Inc., Chicago, Ill.). The level of significance selected for all variables was $p<0.05$. All data are reported as mean±SEM. Representative results are summarized in FIGS. 8-12.

Figure 9:
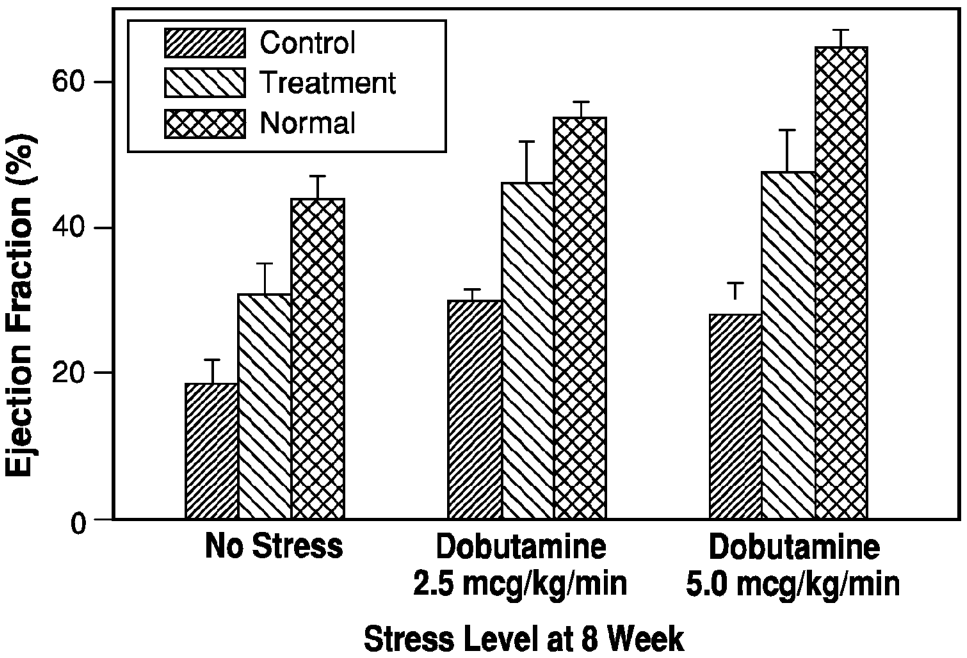
FIG. 9 provides plots of LV ejection fraction determined by stress echocardiography at eight weeks after anteroapical myocardial infarction in sheep.
Figure 10:
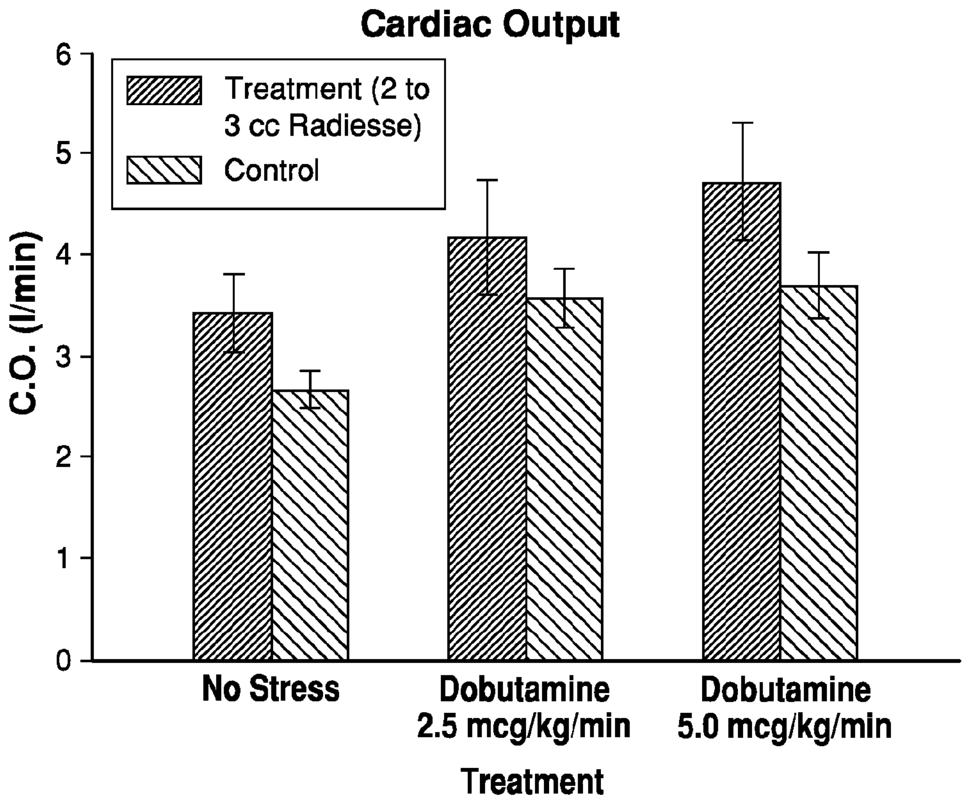
FIG. 10 provides plots of cardiac output measured during dobutamine stress testing.
Figure 11:
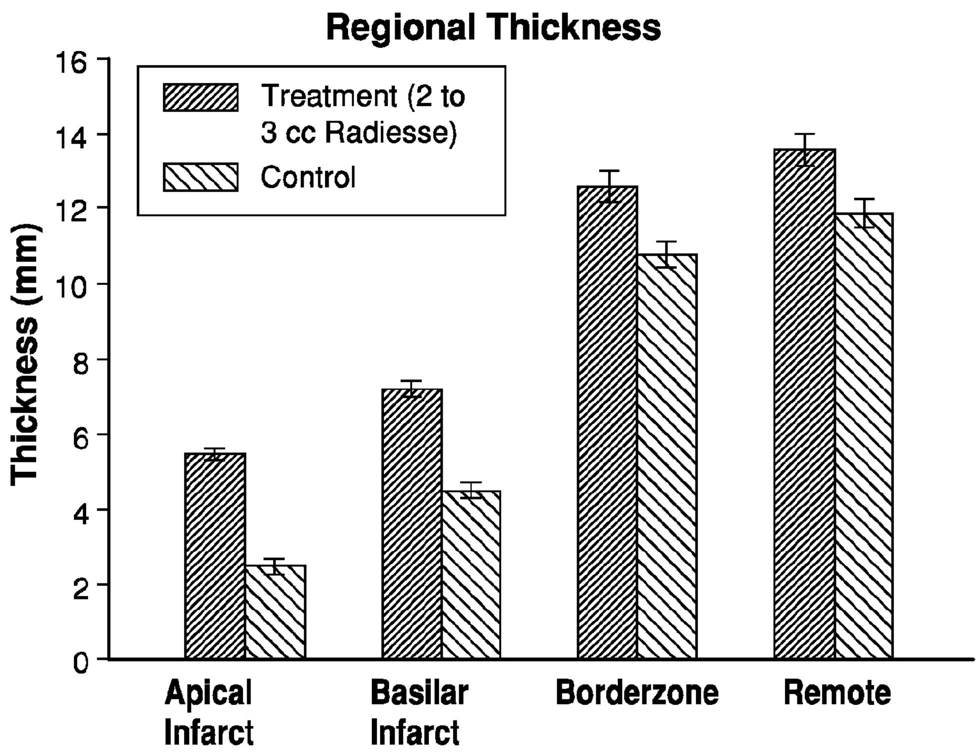
FIG. 11 provides plots of measurements of regional infarct thickness as assessed via postmortem evaluation.

FIG. 8A depicts the LV end diastolic volume determined by stress echocardiography at 8 weeks after anteroapical MI in sheep. These results demonstrate reduction in EDV and improved response to stress in animals injected with Radiesse® immediately after infarction. FIG. 8B provides plots of LV end systolic volume determined by stress echocardiography at 8 weeks after anteroapical myocardial infarction in sheep ("normal" samples refer to uninfarcted tissue). These results demonstrate the reduction in ESV and improved response to stress in animals injected with Radiesse® immediately after infarction. FIG. 9 provides plots of LV ejection fraction determined by stress echocardiography at 8 weeks after anteroapical myocardial infarction in sheep. These results demonstrate increased EF and improved response to stress in animals injected with Radiesse® immediately after infarction ("normal" samples refer to uninfarcted tissue). FIG. 10 provides plots of cardiac output measured during dobutamine stress testing. These results show the association between treatment with volume-increasing material and improved cardiac output and response to stress. FIG. 11 provides plots of measurements of regional infarct thickness as assessed via postmortem evaluation. These results show the association between treatment with volume-increasing material and increased infarct thickness.

Example 6

Histological Analysis of Treated and Untreated Infarct Tissue

Figure 13:
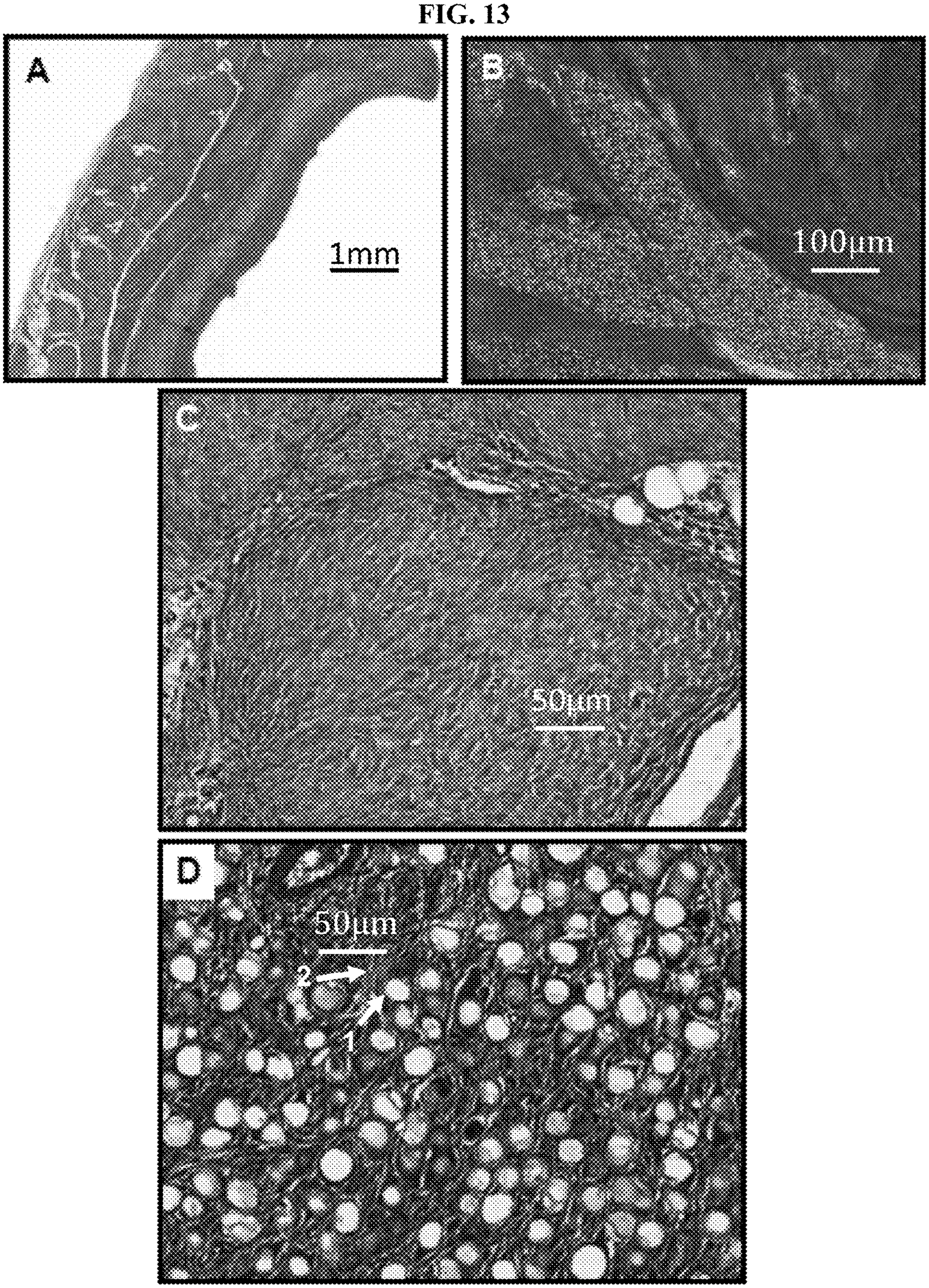
FIG. 13 provides black-and-white images obtained from a Mason trichrome stain of infarct tissue at 2× and 20× magnification from untreated ovine infarct tissue 4 weeks after MI (FIG. 13A, C), and infarcts of the same age injected with 1.3 mL of volume-increasing material (FIG. 13B, D).

FIG. 13 depicts black-and-white images obtained from a Mason trichrome stain of infarct tissue at 2× and 20× magnification from untreated ovine infarct tissue 4 weeks after MI (FIGS. 13A, C), and infarcts of the same age (i.e., 4 weeks after MI) injected with 1.3 mL of volume increasing material (Radiesse®) (FIGS. 13B, D). Histologically the untreated infarcts demonstrated acellular collagenous scar formation. Infarcts treated with Radiesse® volume increasing material contained hydroxyapatite microspheres (FIG. 13B; FIG. 13D, arrow 1) surrounded by a dense cellular infiltrate (FIG. 13B; FIG. 13D, arrow 2).

Untreated infarcts are thin and relatively acellular with occasional islands of residual vacuolated myocytes. Infarcts treated with volume increasing material are thicker with more extensive collagen deposition. The calcium hydroxyapatite microspheres are apparent (FIG. 13D, arrow 1). The carrier agent has been replaced by a dense cellular infiltrate (FIG. 13D, arrow 2).

Without intending to be bound by any particular theory of operation, it appeared as if the increased thickness of the treated infarcts was due to the presence of microspheres and associated cellular response as well as increase in collagen production within the scar.

These results demonstrate, inter alia, that the injection of an acellular, biologically inert material into myocardial infarctions can limit infarct expansion and improve global remodeling, both in the immediate post-MI time period and for extended periods of time following myocardial infarction.

Previous efforts have focused on limiting the remodeling process by reducing early infarct expansion for nearly a decade. Kelley S T et al., *Restraining infarct expansion preserves left ventricular geometry and function after acute anteroapical infarction. Circulation* 1999; 99:135-142. The use of surgical meshes that have covered variable amounts of the LV have been explored to effect this therapeutic goal. Pilla J J et al., *Early post infarction ventricular restraint improves borderzone wall thickening dynamics during remodeling. Ann Thorac Surg* 2005; 80:2257-2262; Enomoto Y et al., *Early ventricular restraint after myocardial infarction: the extent of the wrap determines the outcome of remodeling. Ann Thorac Surg* 2005; 79:881-887; Kelley S T et al., *Restraining infarct expansion preserves left ventricular geometry and function after acute anteroapical infarction. Circulation* 1999; 99:135-142; Moainie S L et al., *Infarct restraint attenuates ischemic mitral regurgitation following posterolateral infarction. Ann Thorac Surg* 2002; 74:444-449.

Most recently the ability of the CorCap Cardiac Support Device (Acorn Cardiovascular, St. Paul, Minn.) to limit early infarct expansion was studied. Pilla J J et al., *Early post infarction ventricular restraint improves borderzone wall thickening dynamics during remodeling. Ann Thorac Surg* 2005; 80:2257-2262; Blom A S et al., *A Cardiac Support Device Modifies Left Ventricular Geometry and Myocardial Structure After Myocardial Infarction. Circulation* 112:1274-1283, 2005. Such experiments consistently demonstrated that mechanical restraint applied early after MI preserves LV function and limits global remodeling in the long-term. Although previous work with external restraining devices has been encouraging, the clinical translation of the approach seems highly unlikely given the necessity of thoracic surgical intervention early in the post-MI period. In contrast, the present invention represents a successful effort to develop a less invasive approach for limiting early infarct expansion.

Recent basic science studies reporting dramatic effects of gene therapy, growth factor administration and cell therapy for heart disease has stimulated the rapid development of sophisticated catheter-based delivery systems. Sherman W et al., *Catheter-based delivery of cells to the heart. Nat Clin Pract Cardiovasc Med* 2006; 3(Suppl. 1):557-564.

In fact, the development of these percutaneous technologies has outpaced the optimization and regulatory approval of most if not all "biologic" therapies for heart disease. These technologies can feasibly be implemented for the non-invasive delivery of acellular, biologically inert materials designed primarily to affect regional mechanical (not biologic) changes within the damaged heart early after MI.

The number of patients that could benefit from this type of intervention is potentially quite large. While reperfusion therapy for acute MI is likely the best method to limit infarct expansion (Force T et al., *Acute reduction in functional infarct expansion with late coronary reperfusion: assessment with quantitative two-dimensional echocardiography. J Am Coll Cardiol* 11:192-200, 1988; Hochman J S, Choo H. *Limitation of myocardial infarct expansion by reperfusion independent of myocardial salvage. Circulation* 75 (1): 299-306, 1987), only about 50% of the 1.1 million episodes of myocardial infarction that occur annually in the United States receive this treatment (see Fox K A A et al., *Decline in Rates of Death and Heart Failure in Acute Coronary Syndromes,* 1999-2006. *JAMA* 297: 1892-1900, 2007) and it is ineffective in restoring microvascular perfusion in nearly one third. Bolognese L et al., *Left ventricular remodeling after primary coronary angioplasty: patterns of left ventricular dilation and long-term prognostic implications. Circulation* 106: 2351-2357, 2002; Bolognese L et al., *Impact of Microvascular Dysfunction on Left Ventricular Remodeling and Long-Term Clinical Outcome after Primary Coronary Angioplasty for Acute Myocardial Infarction. Circulation,* 109:1121-1126, 2004. For the large number of patients that are not offered or do not respond to reperfusion therapy, among others, great benefit could be derived from a minimally invasive, e.g., catheter-based, technique that could affectively limit infarct expansion early after myocardial infarction.

The current disclosure demonstrates, inter alia, the efficacy of a particulate, acellular, volume-increasing to limit infarct expansion when injected directly into the infarct region soon after myocardial infarction. The presently described processes employed with the appropriate mechanical, rheologic and durability parameters to provide long-term protection from prolonged infarct expansion and associated adverse ventricular remodeling.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method for reducing cardiac remodeling comprising: placing directly into a cardiac infarct itself, and optionally into a region of tissue containing the infarct, into tissue adjacent to or partially or completely surrounding the infarct, or both, a composition comprising a biologically compatible, acellular material comprising particles having characteristic dimensions of 25 μm to about 50 μm.

2. The method according to claim 1 comprising placing said composition in said infarct less than about one hour following myocardial infarction.

3. The method according to claim 1 wherein said particles comprise microspheres.

4. The method according to claim 1 wherein said material comprises at least one polymer.

5. The method according to claim 1 wherein said material comprises one or more forms of calcium phosphate.

6. The method according to claim 1 wherein said material comprises a glass or a glass-ceramic.

7. The method according to claim 1 wherein said composition further comprises at least one protein, peptide, or amino acid.

8. The method according to claim 1 wherein said material provides structures that support the growth of fibrous tissue in or near said cardiac infarct tissue.

9. A method for reducing post-infarct cardiac remodeling comprising:

increasing the volume of a cardiac infarct wall via injection of a volume-increasing material comprising particles having characteristic dimensions of about 25 μm to about 50 μm directly into said cardiac infarct itself, and optionally into a region of tissue containing the infarct, into tissue adjacent to or partially or completely surrounding the infarct, or both, and, maintaining substantially all of said material within said cardiac infarct for an extended period of time following said injection.

10. The method according to claim 9 further comprising providing structures that support the growth of fibrous tissue in or near said cardiac infarct.

11. The method according to claim 9 comprising maintaining substantially all of said material within said cardiac infarct for at least about six months following said injection.

12. The method according to claim 9 comprising maintaining substantially all of said material within said cardiac infarct for at least about one year following said injection.

13. The method according to claim 1 wherein said composition further comprises at least one growth factor, enzyme, antibody, or hormone.

* * * * *

UNITED STATES PATENT AND TRADEMARK OFFICE

CERTIFICATE OF CORRECTION

PATENT NO. : 9,238,046 B2
APPLICATION NO. : 12/679147
DATED : January 19, 2016
INVENTOR(S) : Robert C. Gorman et al.

It is certified that error appears in the above-identified patent and that said Letters Patent is hereby corrected as shown below:

In the Specification

Column 1,
Lines 14-22, delete "The United States Government may have rights in the invention described herein, which was made in part with funding from the National Institutes of Health, Grant Nos. HL 63954 and HL 71137 to Robert C. Gorman, HL 76560 to Joseph H. Gorman, III, from the American Heart Association, Post-Doctoral Fellowship No. 0625455U to Robert C. Gorman and Liam P. Ryan, and from individual Established Investigator Awards from the American Heart Association to Robert C. Gorman and Joseph H. Gorman, III." and insert -- This invention was made with government support under grant numbers HL071137, HL076560, and HL063954 awarded by National Institute of Health and from Post-Doctoral Fellowship No. 0625455U and Established Investigator Awards from the American Heart Association Award. The government has certain rights in the invention." --.

Column 8,
Line 24, delete "(NAMED Aesthetics," and insert -- (INAMED Aesthetics, --.

Column 20,
Line 15, delete "3(Suppl. 1):557-564." and insert -- 3(Suppl. 1):S57-S64. --.

In the Claims

Column 22,
Claim 9, line 5, delete "of about 25 μm" and insert -- of 25 μm --.

Signed and Sealed this
Twenty-third Day of August, 2016

Michelle K. Lee
*Director of the United States Patent and Trademark Office*